United States Patent [19]

Krantz et al.

[11] Patent Number: 4,873,232

[45] Date of Patent: Oct. 10, 1989

[54] NOVEL USE FOR CARBAMOYL BENZOATES

[75] Inventors: Alexander Krantz, Toronto, Canada; John M. Young, Redwood City, Calif.

[73] Assignee: Syntex, Palo Alto, Calif.

[21] Appl. No.: 924,246

[22] Filed: Oct. 29, 1986

[51] Int. Cl.$^4$ .................. A61K 31/615; A61K 31/635
[52] U.S. Cl. ..................................... 514/159; 514/166
[58] Field of Search ............................... 514/159, 166

[56] References Cited

U.S. PATENT DOCUMENTS 3,558,571  1/1971  Blume .................................. 260/78

FOREIGN PATENT DOCUMENTS 2241012  3/1973  Fed. Rep. of Germany .
2719020 11/1978  Fed. Rep. of Germany .
  15850 12/1978  Hungary .
 147627  9/1982  Japan .
 171949 10/1982  Japan .
  95338  6/1983  Japan .

OTHER PUBLICATIONS

Blank et al., "Derivatives of Anthranilic Acid," *J. of Chemical and Engineering Data*, 577–579 (1968).
Frost and Hegarty, "Intramolecular Nucleophilic Attack on a Carbamate System by the Ionized Carboxy-Group," *J. Chem. Soc., Chem. Commun.* 3, 82–3 (1973) (submitted with C.A. 78, 110152u 1973)).
Heyman, "Preparation of Isotoates from Isatoic Anhydride," *J. Heterocycl. Chem.*, 15(7), 1131–6 (1978) (submitted with C.A. 90, 38644j 1979)).
Castillo et al., "Reactivity of Bovine Blood Coagulation Factor IX$_{\alpha\beta}$, factor X$_{\alpha\beta}$, and factor XI$_\alpha$ Toward Fluorogenic Peptides Containing the Activation Site Sequences of Bovine factor IX and factor X," *Biochemistry*, 22(5), 1021–9 (1983) (submitted with C.A. 98, 103322j (1983)).
Hedstrom et al., "Suicide Inactivation of Chymotrypsin by Benzoxazinones," *Biochemistry*, 23(8), 1753–9 (1984) (submitted with C.A. 100, 134877h (1984)).
Errede et al., "Acylanthranils" *J. Org. Chem.*, 42(1), 12–18 (1977) (submitted with C.A. 86, 55375g (1977)).
Exner and Lakomy, "Inductive and Mesomeric Effects of Nitrogen and Oxygen Substitutes," *Collect. Czech. Chem. Commun.*, 35(5), 1371–86 (1970) (submitted with C.A. 73, 13977f (1970)).
King and Murch, "Trypanocidal Action and Chemical Constitution," *J. Chem. Soc.*, 125, 2595–611 (1924) (submitted with C.A. 19, 978$^9$ (1925)).
Basterfield and Wright, "Urethans," *J. Am. Chem. Soc.*, 48, 2367–70 (1926) (submitted with C.A. 20, 3164$^3$ (1926)).
Boehm and Mehta, "Esters of Pyrocarbonic Acid," Ber., 71B, 1797–802 (1938) (submitted with C.A. 32, 9043$^4$ (1938)).
Adams et al., "Rutaceous Constituents-13," *Tetrahedron*, 37(1), 209–17 (1981) (submitted with C.A. 95, 150966v (1981)).
Gakhar et al., "Triazolo[4',3':4,5][1,3,4]thiadiazolo[2,3-b]Quinazolin-6-one,"*Monatsh. Chem.*, 114(3), 339–42 (1983) (submitted with C.A. 99, 38434b (1983)).
Hegarty et al., "Cyclizations Involving Oxyanions as Nucleophiles Towards the Carbamate Linkage in the Rate-Determining Step," *J. Chem. Soc., Perkin Trans. 2*, 10, 1249–57 (1974) (submitted with C.A. 82, 85612s (1975)).
Johnson, "Structure–Activity Relationships for Substrates and Inhibitors of Hen Brain Neurotoxic Esterase," *Biochem. Pharm.* 24, 797–805 (1975) (submitted with C.A. 83, 188903n (1975)).
Hall, "Field and Inductive Effects on the Base Strengths of Amines," *J. Am. Chem. Soc.*, 78, 2570–2 (1956) (submitted with C.A. 51, 1164c (1957)).
Najer et al., "New Carbamate Derivatives of p-Aminobenzoic Acid Showing Local Surface Anesthetic Activity," *Bull. Soc. Chim. France*, 1189–92 (1955) (submitted with C.A. 51, 10424f (1957)).
Iwakura et al., "The Syntheses and Some Reactions of ω-Isocyanatoalkanecarboxylic Acid Chlorides and Isocyanatobenzoyl Chlorides," *J. Org. Chem.*, 31(1), 142–6 (1966) (submitted with C.A. 64, 6551d (1966)).
Smith et al., "Acyl-Enzymes as Thrombolytic Agents in a Rabbit Model of Venous Thrombosis," *Thromo. Haemostasis*, 47(3), 269–74 (1982) (submitted with C.A. 97, 120123s (1982)).

Primary Examiner—Stanley J. Friedman
Attorney, Agent, or Firm—Lester E. Johnson; Tom M. Moran; Alan M. Krubiner

[57] ABSTRACT

Novel alkoxycarbonylamino benzoates and related compounds (carbamoyl benzoates) are disclosed for treatment of auto-immune disease states, such as arthritis.

30 Claims, No Drawings

NOVEL USE FOR CARBAMOYL BENZOATES

BACKGROUND OF THE INVENTION

1. Field of the Invention

This invention relates to the use of carbonyl amino benzoates for treatment of auto-immune diseases in humans and animals; and pharmaceutical compositions comprising a carbonyl amino benzoate and at least one pharmaceutical excipient.

2. Related Art

U.S. patent application Ser. No. 748,631, filed Jun. 25, 1985, and assigned to the assignee of this invention, discloses that compounds of the following Formula:

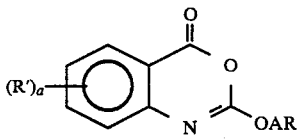

wherein:
  a is an integer of 0-4;
  A is a bond, or alkylene having one to eight carbon atoms;
  R is hydrogen, phenyl, imidazolyl or cycloalkyl having three to six carbon atoms, wherein the phenyl, imidazolyl or cycloalkyl ring is optionally substituted with 1-3 substituents independently selected from the group consisting of lower alkyl having one to four carbon atoms, lower alkoxy having one to four carbon atoms, $-N(R^1)_2$, $-NO_2$, halo or lower alkylthio having one to four carbon atoms, and,
  each R' is independently selected from the group consisting of lower alkyl having one to six atoms, lower alkenyl having two to six carbon atoms, lower alkoxy having one to six carbon atoms, lower alkylthio or halo-lower alkyl having one to four carbon atoms, halo, $-NO_2$, $-N(R^1)_2$, $-NR^1COR^2$, $-NR^1COR^2$, and

in which
  each $R^1$ is independently hydrogen or lower alkyl having one to four carbon atoms, or together form a piperidine or a piperazine ring optionally substituted at the ring nitrogen by lower alkyl having one to four carbon atoms or $-CH_2CH_2OH$,
  each $R^2$ is independently lower alkyl having one to four carbon atoms,
  A is an alkylene group if R is hydrogen, and the pharmaceutically acceptable acid addition salts thereof, are useful as serine protease inhibitors in humans and animals. U.S. patent application Ser. No. 748,631 is hereby fully incorporated by reference into this disclosure.

Many chronic, inflammatory conditions of man and animals fluctuate in intensity with concomitant fluctuations in pain and swelling. While the acute symptoms of many of the rheumatic diseases, such as rheumatoid arthritis, may be controlled by the administration of analgesic, anti-inflammatory drugs such as aspirin and aspirin-like drugs, the underlying disease process is not affected. Tissue destruction in diseases such as rheumatoid arthritis, encephalomyelitis, multiple sclerosis, type II diabetes and the like, proceeds inexorably in the face of palliative treatment with aspirin-like drugs, and results, eventually, in substantial and debilitating loss of function.

Since many chronic, inflammatory conditions of man and animals are now known to result from an attack by the body's immune system on some portion or tissue of the body (a situation called auto-immunity), attempts have been made to treat such diseases with agents which suppress the function of the immune system. Cortico-steroids, for example, suppress the ability of the body to mount an effective immune response. Cortico-steroids are non-selective in this respect and suppress both humoral (antibody) and cell-mediated (delayed type hypersensitivity) responses, although only one or the other response may be involved in a particular auto-immune disease. Corticosteroids find some utility in controlling acute flares of auto-immune diseases, but they are not curative and the potential for side effects precludes their extended use. Similarly, immunosuppressive drugs derived from cancer chemotherapy, such as cyclophosphamide and methotrexate, find certain utility in treatment of auto-immune diseases, and on rare occasions may even produce long term remission.

Nevertheless, these drugs are also non-selective and suppress all aspects of the immune system. During their administration the body is rendered incapable of mounting effective resistant to invading micro-organisms (viruses, bacteria, fungi, yeasts, protozoa), and life-threatening infections are a frequent result. Additionally, prolonged use of the general immuno-suppressive agents results in an increased incidence of various cancers.

Significant therapeutic advances in the treatment of auto-immune diseases requires the discovery and use of agents which are much more selective in their effects on the immune response system: i.e., agents which suppress only those processes involved in a particular disease, leaving the remaining processes unaffected and competent to combat infectious diseases and the like.

At an early stage of discovery, since drugs cannot be tested directly in man, recourse is had to testing or screening in animal models of inflammation and auto-immune disease. Such models include:

1. Carrageenan-induced paw edema in the rat. This is a non-specific model of acute inflammation which does not involve the immune system. A solution of carrageenan injected into the foot pad of a rat causes reddening, swelling and pain which is maximal three to six hours after administration and then resolves. Aspirin-like drugs and corticosteroids administered at the appropriate doses effectively inhibit the inflammatory response caused by the carrageenan injection. Immunosuppressive agents are not effective under these circumstances.

2. Adjuvant-induced arthritis in the rat. This is an immune-based animal model of rheumatoid arthritis and other rheumatic diseases. A mixture of Freund's Complete Adjuvant (consisting of saline, mineral oil, and the dried, killed micro-organism Mycobacterium butyricum) is injected into the skin of a rat. An initial, local inflammatory response (1 to 4 days) is followed by a generalized inflammatory condition (day 9 onwards) in which the animal mounts an immune response against its own cartilaginous tissues. The disease process is particularly evident in peripheral joints which show reddening, swelling and tenderness. Inflammatory cells invade these joints, and release enzymes and other factors which produce much tissue destruction. As the disease progresses, both joints and underlying bone are destroyed such that loss of mobility results. It is believed that both humoral (anti-body) and cell-mediated immunity may be involved in this model. All manifestations of this disease in rats are effectively controlled by daily administration of appropriate doses of corticosteroids, cyclophosphamide and aspirin-like drugs. Whereas aspirin-like drugs effectively prevent tissue destruction resulting from this induced disease in rats, they are not effective in preventing the tissue destruction associated with the inexorable course of rheumatoid arthritis in man.

3. Experimental allergic encephalomyelitis in the rat. This is an immune-based animal model of demyelinating diseases which shows resemblance to multiple sclerosis. A mixture of syngeneic spinal cord homogenate in Freund's Complete Adjuvant injected subcutaneously into the rat induces an anti-immune response directed against the myelin covering the nerves of the central nervous system. Beginning nine days after the injection, the rat begins to lose body weight and between the twelfth and sixteenth day shows symptoms of paralysis which may be as mild as urinary incontinence and tail flaccidity or as severe as complete body paralysis. These symptoms result from attack of immune cells on the nerves with subsequent destruction and loss of ability to transmit the nervous impulses necessary for controlling muscle function. Daily treatment with cyclophosphamide (starting on the first day) gives protection from the weight loss and paralysis suffered by the animals. This is consistent with the general immuno-suppressive effects of this drug. Corticosteroid treatment also prevents the appearance of paralytic symptoms, but the dose of corticosteroid required is such that the corticosteroid itself causes weight loss greater than that produced by the disease alone. In contrast to their action in Adjuvant-induced Arthritis in the rat, aspirin-like drugs are completely ineffective in preventing the symptoms and weight loss of experimental allergic encephalomyelitis.

SUMMARY OF THE INVENTION

A first aspect of the invention is a method for treating auto-immune diseases, by administering to a subject in need thereof a compound of the formula:

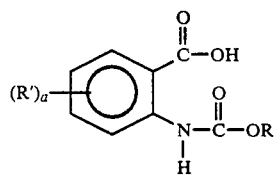

(I)

or a pharmaceutically acceptable salt thereof, wherein:
a is an integer of 0 to 4;
R is alkyl, phenyl, (imidazol-4-yl)methyl or cycloalkyl having three to six carbon atoms, wherein the phenyl or cycloalkyl ring is optionally substituted with 1 to 3 substituents independently selected from the group consisting of lower alkyl having one to four carbon atoms, lower alkoxy having one to four carbon atoms, $-N(R^1)_2$, $-NO_2$, halo, and lower alkylthio having one to four carbon atoms;

and each R' is independently selected from the group consisting of hydroxy, lower alkyl having one to six carbon atoms, lower alkenyl having two to six carbon atoms, lower alkoxy having one to six carbon atoms, halo-lower alkyl or lower alkylthio having one to six carbon atoms, halo,

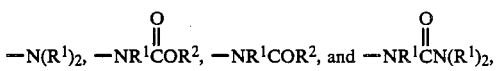

in which
each $R^1$ is independently hydrogen or lower alkyl having one to four carbon atoms, or together form a piperidine or piperazine ring optionally substituted at the ring nitrogen with lower alkyl having one to four carbon atoms or $-CH_2CH_2OH$;
each $R^2$ is independently lower alkyl having one to four carbon atoms.

A second aspect of the invention is a pharmaceutical composition which comprises a therapeutically effective amount of a compound of Formula (I), or a pharmaceutically acceptable salt thereof, in admixture with at least one pharmaceutically acceptable excipient.

DETAILED DESCRIPTION

Definitions

As used herein:

"Alkoxy" means the group $-OR$, where R is lower alkyl as defined herein.

"Alkyl" means a branched or unbranched saturated hydrocarbon chain having, unless otherwise noted, 1 to 12 carbon atoms.

"Alkylene" means a branched or unbranched saturated hydrocarbon bridging group having one to eight carbon atoms, including but not limited to, methylene, ethylene, propylene, isopropylene, n-propylene, butylene, sec-butylene, isobutylene, n-pentylene, hexylene, octylene, and the like.

"Auto-immune diseases" are to be understood as diseases which result from an attack by the host's immune system on a tissue or portion of the host, including such diseases as arthritis and multiple sclerosis.

"Carbamoyl benzoates" as used herein refers generically to alkoxycarbonylamino benzoates, phenoxycarbonylamino benzoates, and phenyl-lower-alkoxycarbonylamino benzoates of Formula I.

"Halo" refers to chloro, bromo and iodo.

"Halo-lower alkyl" means a lower alkyl radical, bearing one or two halo substituents. Examples include but are not limited to bromomethyl, dibromomethyl, chloroethyl, dichloroethyl, and the like.

"Lower alkyl" means a branched or unbranched saturated hydrocarbon chain having, unless otherwise noted, one to six carbon atoms, including but not limited to methyl, ethyl, propyl, isopropyl, n-propyl, n-butyl, sec-butyl, isobutyl, tert-butyl, n-pentyl and positional isomers thereof, n-hexyl and positional isomers thereof, and the like. Lower alkyl groups may be limited to fewer than six carbon atoms when specifically designated, e.g. "$R^2$ is lower alkyl having one to four carbon atoms."

"Lower alkenyl" means a branched or unbranched unsaturated hydrocarbon chain of 2 to 6 carbon atoms, including but not limited to vinyl, allyl, 1-propenyl, isopropenyl, 1-butenyl, 2-butenyl, isobutenyl, 1,3-butadienyl, 1-pentenyl, 2-pentenyl, isoprenyl, 1-hexenyl, 2-hexenyl, 3-hexenyl, cis-2-butenyl, trans-2-butenyl, cis-2-pentenyl, trans-2-pentenyl, 3-methyl-1-butenyl, 2-methyl-2-butenyl and 2,3-dimethyl-2-butenyl.

"Lower alkoxy" means the group —OR wherein R is lower alkyl as herein defined.

"Lower alkylthio" means the group —SR wherein R is lower alkyl as herein defined.

"Optional" or "optionally" means that the subsequently described event or circumstances may or may not occur, and that the description includes instances where said event or circumstance occurs and instances in which it does not. For example, "phenyl . . . optionally substituted" means that the phenyl may or may not be substituted and that the description includes both unsubstituted phenyl and phenyl wherein there is substitution.

"Pharmaceutically acceptable salt" refers to those salts which retain the biological effectiveness and properties of the free acids and which are not biologically or otherwise undesirable. Such salts are prepared by conventional techniques by treating the free acid with pharmaceutically acceptable non-toxic bases, including metal salts such as sodium, potassium, calcium, aluminum and the like, as well as organic amine salts, such as triethylamine, 2-dimethylamino ethanol, 2-diethylaminoethanol, lysine, arginine, histidine, caffeine, procaine, N-ethylpiperidine, hydrabamine, choline, betaine, ethylenediamine, glucosamine, methylglucamine, theobromine, purines, piperazine, piperidine, N-ethylpiperidine, polyamine resins, and the like. The reaction is conducted in water, alone or in combination with an inert, water-miscible organic solvent, at a temperature of from about 0° C. to about 100° C., preferably at room temperature. Typical inert, water-miscibile organic solvents include methanol, ethanol, isopropanol, butanol, acetone, dioxane or tetrahydrofuran. The molar ratio of compounds of Formula I to base used are chosen to provide the ratio desired for any particular salt. For preparing, for example, the calcium salts or magnesium salts the free acid starting material of Formula I can be treated with at least one-half molar equivalent of pharmaceutically acceptable base to yield a neutral salt. When the aluminum salts of the compounds of Formula I are prepared, at least one-third molar equivalent of the pharmaceutically acceptable base are employed if a neutral salt product is desired.

The salt derivatives of the compounds of Formula I can be reconverted to their respective free acids by acidifying said salts with an acid, preferably an inorganic acid, e.g., hydrochloric acid, sulfuric acid, and the like, at temperature of from about 0° C. to about 50° C., preferably at room temperature.

Salts of the compounds of Formula I may be interchanged by taking advantage of differential solubilities of the salts, volatilities or acidities of the acids, or by treating with the appropriately loaded ion exchange resin. For example, the interchange is effected by the reaction of a salt of the compounds of Formula I with a slight stoichiometric excess of an acid of a lower pKa than the acid component of the starting salt. This conversion is carried out at a temperature between about 0° C. and the boiling point of the solvent being used as the medium for the procedure.

"Phenyl lower alkyl" means a phenyl radical bonded to a lower alkyl radical, which is in turn bonded to the structure shown. Examples are benzyl, phenylethyl, and the like.

When reference is made to compounds of U.S. patent application Ser. No. 748,631, for example as starting materials for compounds of Formula (I) herein, the substituents have the definitions given in U.S. patent application Ser. No. 748,631, unless otherwise noted.

Certain of the compounds described herein have chiral centers and exist as optical antipodes. The invention described and claimed herein includes the use of each of the individual enantiomers as well as their racemic modifications and the racemic mixture.

The compounds of Formula (I) are named as substituted benzoic acids, numbered as follows:

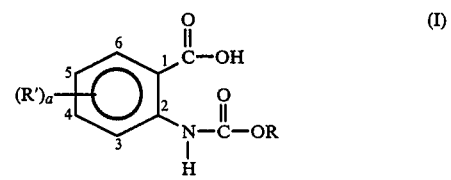

Precursors of the compounds of this invention are named as 2-oxy-4H-3,1-benzoxazin-4-ones using the numbering system set forth below.

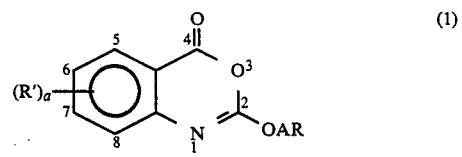

Preferred Embodiments

Within the broadest scope of the method of this invention, the use of certain subgroups of the compound of Formula (I) is preferred. For example, preferred subgroups are compounds of Formula (I) in which a is at least one. Among these, preferred classes encompass compounds in which the R's are in the 6- and/or 4-positions. Within these classes, preferred subclasses include compounds of Formula (I) in which an R' is in the 6-position; of these, especially preferred are compounds of Formula (I) in which an R' is also in 4-position.

Preferred R' substituents at the 6- position are lower alkyl having one to six carbon atoms and lower alkenyl having two to six carbon atoms. Especially preferred R' substituents at the 6- position are lower alkyl having one to six carbon atoms, particularly one to three carbon atoms, and most particularly methyl or ethyl. Preferred R' substituents at the 4- position are hydroxy, lower alkoxy having one to six carbon atoms,

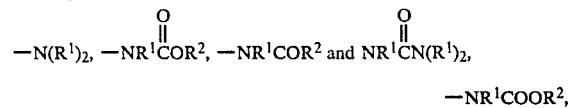

particularly —N(R$^1$)$_2$ and especially where each R' is independently hydrogen, methyl or ethyl, and R$^2$ is methyl or ethyl.

At the present time, the most preferred compounds used in the method and composition of this invention are:
2-ethoxycarbonylamino-6-isopropylbenzoic acid;
2-methoxycarbonylamino-6-isopropylbenzoic acid;
2-ethoxycarbonylaminobenzoic acid;

2-benzyloxycarbonylaminobenzoic acid;
2-ethoxycarbonylamino-4,5-dimethoxybenzoic acid;
2-benzyloxycarbonylamino-4,5-dimethoxybenzoic acid;
2-methoxycarbonylamino-6-methylbenzoic acid;
2-ethoxycarbonylamino-6-methylbenzoic acid;
2-propoxycarbonylamino-6-methylbenzoic acid;
2-isobutoxycarbonylamino-6-methylbenzoic acid;
2-benzyloxycarbonylamino-6-methylbenzoic acid;
2-methoxycarbonylamino-6-ethylbenzoic acid;
2-ethoxycarbonylamino-6-ethylbenzoic acid;
2-propoxycarbonylamino-6-ethylbenzoic acid;
2-methoxycarbonylamino-6-propylbenzoic acid;
2-ethoxycarbonylamino-6-propylbenzoic acid; and
2-propoxycarbonylamino-6-propylbenzoic acid.

Utility, Dosage and Administration

Agents which might be useful in treating autoimmune disorders, such as rheumatoid arthritis and multiple sclerosis, are considered to be those which show a selectivity with respect to suppressing particular aspects of the immune response, a greater safety margin than the existing therapeutic agents, or both. Unexpectedly, we have found a class of agents comprising the carbamoyl benzoates of Formula (I), which, when administered daily to rats at effective oral doses, provide significant protection against the symptoms and weight loss associated with Experimental Allergic Encephalomyelitis. In contrast to the generally immuno-suppressive agents such as corticosteroids (dexamethosone) and cyclophosphamide, the carbamoyl benzoates are not effective in the Adjuvant-induced Arthritis. This indicates that the carbamoyl benzoates of this invention exhibit a desirable, selective effect on the immune system.

Furthermore, although the agents of this invention show some similarity to flufenamic acid (an aspirin-like drug which has analgesic and acute anti-inflammatory activity), the carbamoyl benzoates are relatively ineffective against Carrageenan-inducted paw edema in the rat and free from the gastro-intestinal (ulcerogenic) effects associated with aspirin-like drugs such as flufenamic acid.

Administration of the active compounds and salts described herein can be via any of the accepted modes of administration for systemically active therapeutic medicaments. These methods include oral, parenteral and otherwise systemic, aerosol or topical forms.

Depending on the intended mode of administration, the compositions used may be in the form of solid, semi-solid or liquid dosage forms, such as, for example, tablets, suppositories, pills, capsules, powders, liquids, aerosols, suspensions, or the like, preferably in unit dosage forms suitable for single administration of precise dosages. The compositions will include a conventional pharmaceutical carrier or excipient and an active compound of Formula I or a pharmaceutically acceptable salt thereof and, in addition, may include other medicinal agents, pharmaceutical agents, carriers, adjuvants, etc.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pennsylvania, 17th Edition, 1985. The composition or formulation to be administered will, in any event, contain a quantity of the active compound(s) in an amount effective to alleviate the symptoms of the subject being treated.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

For the compounds of Formula I, either oral or nasal (bronchial) administration is preferred, depending on the nature of the disorder being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions can contain about 1% to about 95% active ingredient, preferably about 25% to about 70%.

Oral and nasal administration to the lungs can also be effected by aerosol delivery forms. For aerosol administration, the active ingredient is preferably supplied in finely divided form along with a surfactant and a propellant. Typical percentages of active ingredients are 0.01 to 20% by weight, preferably 0.04 to 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark "Spans") and the polyoxyethylene and polyoxypropylene derivatives of these esters. Mixed esters, such as mixed or natural glycerides may be employed. The preferred surface-active agents are the oleates or sorbitan, e.g., those sold under the trademarks "Arlacel C" (Sorbitan sesquioleate), "Span 80" (sorbitan monooleate) and "Span 85" (sorbitan trioleate). The surfactant can constitute about 0.1 to about 20% by weight of the composition, preferably about 0.25 to about 5%.

The balance of the composition is ordinarily propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the trademark "Freon." Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

For topical administration, these compositions comprise an effective amount of a compound of this class in admixture with a pharmaceutically acceptable nontoxic carrier. A suitable range of composition would be about 0.1% to about 10% active ingredient, and the balance carrier, preferably 1 to about 2% active ingredient. The concentration of active ingredient in pharmaceutical compositions suitable for topical application will vary depending upon the particular activity of the compound used in conjunction with the condition and subject to be treated. Suitable carriers or medicament vehicles for topical application of these compounds include creams, ointments, lotions, emulsions, solutions and the like.

For example, a suitable ointment for topical application of compounds of the invention contains 15 to 45 percent of a saturated fatty alcohol having 16 to 24 carbon atoms such as cetyl alcohol, stearyl alcohol, behenyl alcohol, and the like and 45 to 85 wt. percent of a glycol solvent such as propylene glycol, polyethylene glycol, dipropylene glycol, and mixtures thereof. The ointment can also contain 0 to 15 wt. percent of a plasticizer such as polyethylene glycol, 1,2,6-hexanetriol, sorbitol, glycerol, and the like; 0 to 15 wt. percent of a coupling agent such as a saturated fatty acid having from 16 to 24 carbon atoms, e.g., stearic acid, palmitic acid, behenic acid, a fatty acid amide e.g., oleamide, palmitamide, stearamide, behenamide and an ester of a fatty acid having from 16 to 24 carbon atoms such as sorbitol monostearate, polyethylene glycol monostearate, polypropylene glycol or the corresponding monoester of other fatty acids such as oleic acid and palmitic acid; and 0 to 20 wt. percent of a penetrant such as dimethyl sulfoxide or dimethylacetamide.

The amount of active compound administered will of course, be dependent on the subject being treated, the severity of the affliction, the manner of administration and the judgment of the prescribing physician. However, an effective dosage is in the range of about 0.01 to about 100 mg/kg/day; preferably about 0.5 to about 50 mg/kg/day, and most preferably from about 5 to about 10 mg/kg/day.

Methods of Preparation

The compounds used in the method of the present invention are generally made by hydrolyzing compounds of the formula:

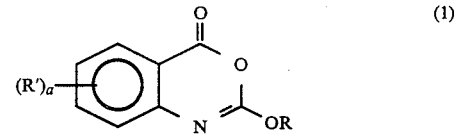

where the substituents are defined as in the Summary of the invention. Methods for making the compounds of Formula (1) herein are disclosed, as methods for making compounds of "Formula (I)," in U.S. patent application Ser. No. 748,631, filed on Nov. 8, 1985, and assigned to the assignee of the present invention. This U.S. patent application Ser. No. 748,631 is hereby fully incorporated into the present application by reference.

Thus, the present disclosure will focus on the preparation of the compounds of Formula (I) of this disclosure from the compounds of Formula (1) as starting materials, except in such cases where alternative synthetic routes have been used. Additionally, for the purposes of illustration, the formation of the precursor benzoxazinones of Formula (1) will be outlined in Reaction Scheme I, although this information is also available in U.S. patent application Ser. No. 748,631, incorporated herein by reference.

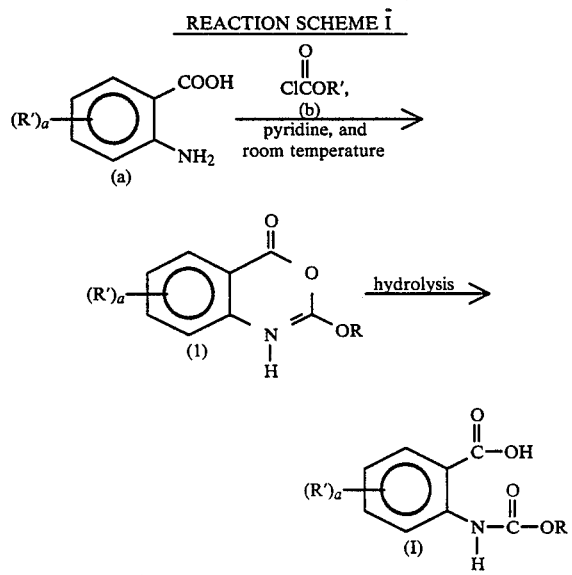

As outlined in Reaction Scheme I, the compounds of Formula (1) are prepared by derivatization and cyclization of the corresponding appropriately substituted or unsubstituted 2-aminobenzoic acid of Formula (a). Cyclization is preferably achieved by reaction of the chosen aminobenzoic acid with about 2.5 to about 4, preferably about 3 equivalents of the desired chloroformates of Formula (b), ClCOOR', wherein R' is alkyl, phenyl, or phenyl lower alkyl. The reaction takes place in an inert solvent such as dichloromethane or tetrahydrofuran in the presence of a tertiary amine such as triethylamine or pyridine, or, preferably, in pyridine without any co-solvent, and is carried out at room temperature over a period of about 0.5 to about 5 hours, preferably about 1 to about 3 hours. The product, a compound of Formula (1), is then isolated by conventional means.

Isolation and purification of the final compounds and intermediates described herein can be effected, if desired, by any suitable separation or purification procedure such as, for example, filtration, extraction, crystallization, column chromatography, thin-layer chromatography, thick layer chromatography, or a combination of these procedures. Specific illustrations of suitable separation and isolation procedures can be had by reference to the Examples. However, other equivalent separation or isolation procedures could, of course, also be used.

Unsubstituted 2-aminobenzoic acid is readily commercially available. The substituted 2-aminobenzoic acids (Formula (a)) used in preparing the compounds used in this invention are either commercially available, or can be prepared by methods well known in the art. The commercially available 2-aminobenzoic acids include 2-amino-6-methyl-benzoic acid. A list of commercially available 2-aminobenzoic acids is available in *Chem. Sources*-U.S.A., 26th Ed., 1985, Directories Publishing Company, Inc., Ormond Beach, Florida. Appropriately substituted 2-aminobenzoic acids which are not commercially available can be readily prepared by methods known in the art. Suitable methods include those of B. R. Baker, *et al., J. Org. Chem.*, 17, 141, (1952) and of L. A. Paquette, *et al., J. Am. Chem. Soc.* 99, 3734, (1981). The former method involves the preparation of an isatin from a substituted aniline derivative, followed by subsequent oxidatin of the isatin to yield the 2-aminobenzoic acid, as illustrated in Preparation I, below. The latter procedure employs the reduction of the corresponding aromatic nitro- derivative to the 2-aminobenzoic acid.

The alkyl, phenylalkyl or phenyl chloroformates of Formula (b) are either commercially available, or can be prepared by methods well known or readily available in the chemical literature. Commercially available chloroformates include methyl chloroformate, ethyl chloroformate, n-butyl chloroformate and isobutyl chloroformate. Suitable chloroformates which are not commercially available can be prepared by known methods. Preparative methods include those of D. H. R. Barton et al., J. Chem Soc. 18 55–1857 (1968) and K. Kurita et al., J. Org Chem. 41, 2070–2071, (1976). The former method involves treatment of an appropriate alcohol with phosgene in an inert solvent such as anhydrous ether. Further description of this method is provided in Preparation II, below. The latter procedure involves the reaction of an appropriate alcohol with trichloromethyl chloroformate (diphosgene) in dry dioxane at refluxing temperature.

As outlined in Reaction Scheme I, the compounds of Formula (I) are prepared by hydrolysis of the compounds of Formula (1). This hydrolysis method will work for all compounds of Formula (1) made by Reaction Schemes I through IX of U.S. patent application Ser. No. 748,631.

The hydrolysis can be either an acid or a base hydrolysis. For example, an alkali hydroxide base, such as sodium hydroxide or potassium hydroxide, can be used in an aqueous solution. By way of example, a 2 to 4% sodium hydroxide solution can be used. A water miscible solvent such as DME, THF, or dioxane can be used as a co-solvent. The reaction time is generally in the range of from about 1 to about 8 hours at room temperature.

However, the hydrolysis is preferably an acid hydrolysis. Most acids can be used, including mineral and organic acids, such as $H_2SO_4$, $H_3PO_4$, $CF_3COOH$, and $CH_3COOH$. However, hydrolysis is most preferably achieved by dilute mineral acid in an organic solvent, preferably 4N HCl in tetrahydrofuran (THF) or dioxane. The hydrolysis is most preferably carried out at a temperature in the range of from about 5° to about 30° C., most preferably at room temperature. The reaction time can vary considerably, e.g., from about 10 minutes to about 15 hours, but is preferably about 10 to about 30 minutes, and most preferably about 15 minutes. The final product, a compound of Formula (I), is then isolated by conventional means.

REACTION SCHEME II

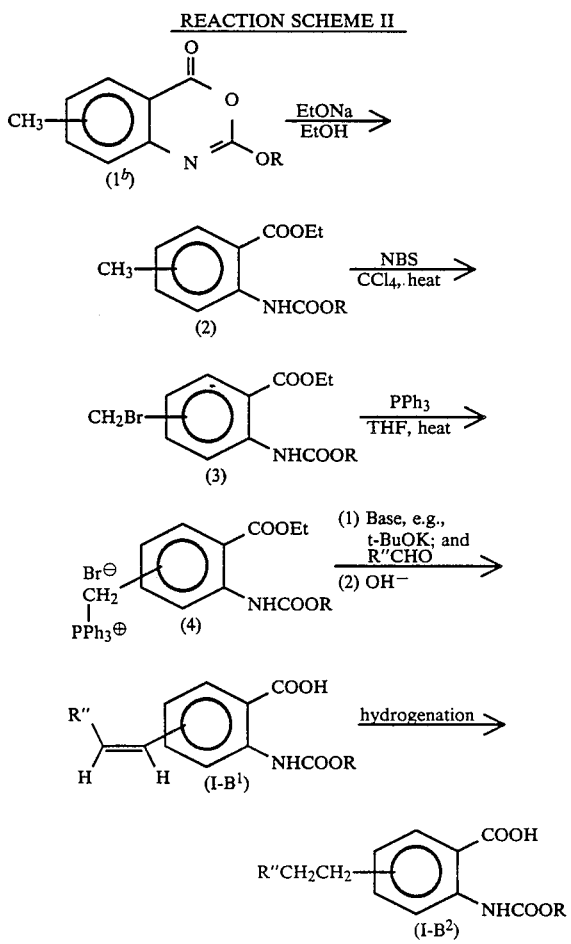

R = lower alkyl, phenyl, or phenyl lower alkyl.

R" = H, methyl, ethyl, propyl, butyl, and isomers.

As noted above, the starting material of Formula ($1^b$) is fully taught in U.S. patent application Ser. No. 748,631, fully incorporated by reference herein. Reaction Scheme II provides an alternative method to prepare the compounds of Formula (I) in cases where the anthranilic acid starting materials of Formula (1) are less accessible.

As outlined in Reaction Scheme II, 2-ethoxycarbonylamino-6-methylbenzoate (2) is prepared by using a base, preferably sodium ethoxide, to open the right-hand ring of benzoxazinone ($1^b$). The pH for this step in the Reaction Scheme is in the range of about 7.5 to 12, preferably about pH 8.5. The reaction is carried out at a temperature in the range of about −15° C. to about room temperature, preferably about 0° C. Alcohol, such as absolute ethanol, is preferred as solvent. The reaction is allowed to proceed for a period of several hours, preferably about two hours.

Benzylic bromination of (2) is preferably carried out with one equivalent of N-bromosuccinimide (NBS), in the presence of a catalytic amount (i.e., less than about 10% by weight, and preferably about 2% to about 5% by weight) of a radical initiator, such as a peroxide (usually dibenzoyl peroxide), or preferably an azo compound 2,2-azobisisobutylnitrile (AIBN). Light can also be used to initiate the reaction. The reaction is carried out in a nonpolar organic solvent, preferably carbon tetrachloride, under refluxing conditions for about 1 to about 5 hours, preferably about 2 hours.

The resulting benzyl bromide derivative (3) is refluxed with a slight excess of triphenylphosphine (PPh₃) in an organic solvent, preferably tetrahydrofuran (THF), for about 4 hours under anhydrous conditions, to yield the phosphonium bromide (4) as a white precipitate.

The phosphonium bromide (4) can be condensed at 0° C. without purification, at a temperature of between about 15° C. to about room temperature, and preferably at about 0° C., with an aldehyde of formula RCHO, where R is H or lower alkyl, in the presence of about two equivalents of strong base, preferably potassium t-butoxide, to give the corresponding olefinic benzoate. The olefinic benzoate can be hydrolyzed without isolation with a base such as NaOH at a pH in the range of about 8 to about 12 preferably at about pH 10, in water or in some cases in aqueous DMSO solution, to give the expected olefinic acid (I—B¹) in 20 to 30% overall yield from benzyl bromide derivative of Formula (3).

Finally, the 2-alkoxycarbonylamino-6-alkyl benzoic acids of Formula (I—B²), and the 2-phenoxycarbonylamino and 2-phenyl lower alkoxycarbonylamino analogs of Formula (I—B²), can be prepared by hydrogenation, preferably catalytic hydrogenation, of the corresponding olefinic benzoic acid of Formula (I—B¹). Any of a variety of catalysts can be used, such as Pt-C or Rh-C. However, hydrogenation of the corresponding olefinic benzoic acid is preferably accomplished with catalytic amount (i.e., less than about 10% by weight, and preferably 5% by weight) of 10% Pd-C (Aldrich) under H₂ pressure in a range from about 10 to about 100 psi, preferably 40 psi in a Parr reactor. The reaction is preferably carried out in alcohol, most preferably ethanol, at a temperature in a range of from about 5° C. to about 40° C., most preferably at room temperature, for a period of about 10 to about 20 hours, normally about 15 hours.

Isolation and purification of the final compounds and intermediates described herein can be effected, if desired, by any suitable separation or purification procedure such as, for example, filtration, extraction, crystallization, column chromatography, or a combination of these procedures. Specific illustrations of suitable separation and isolation procedures can be had by reference to the examples hereinbelow. However, other equivalent separation or isolation procedures could, of course, also be used.

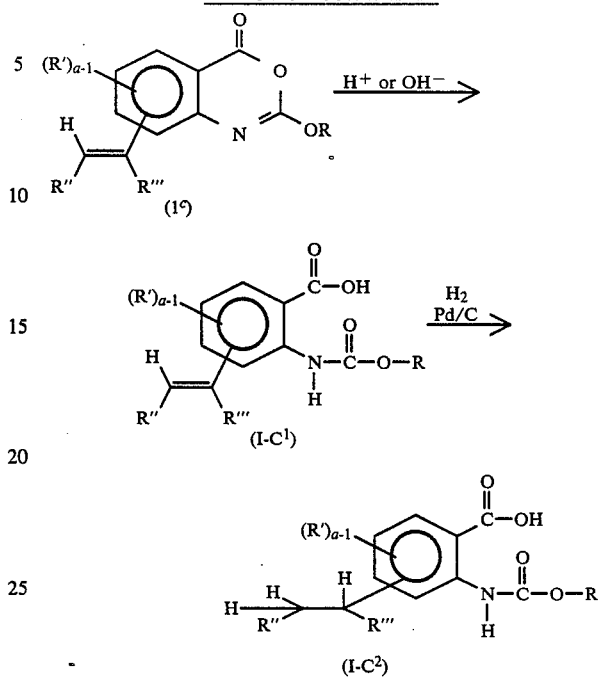

Reaction Scheme III is used where the starting material of Formula (1) is that product designated Formula (IG₃) in U.S. patent application Ser. No. 748,631, and designated Formula (1ᶜ) here. This starting material can be hydrolyzed to the free acid with dilute acid or hydroxide solution. The product can be isolated by standard means. The benzoic acid of Formula (I—C¹) is further converted to the saturated compound of Formula (I—C²) by catalytic hydrogenation, for example, over 10% Pd/C at about 50 psi hydrogen.

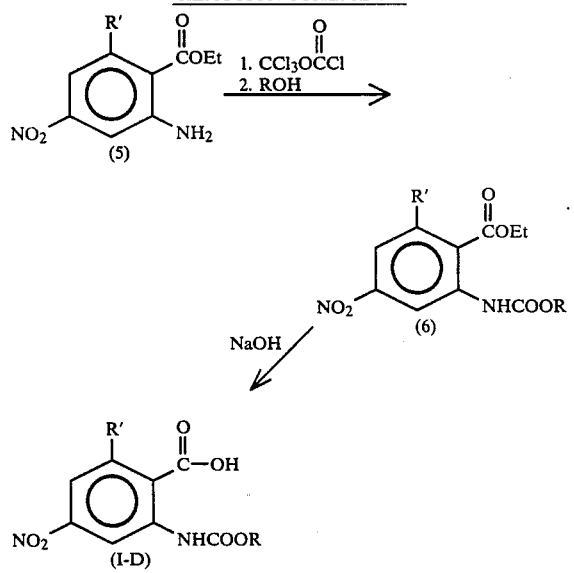

As shown in Reaction Scheme IV, the appropriately substituted ethyl anthranilate of Formula (5), designated as Formula (VIII) in U.S. patent application Ser. No. 748,631, is converted to the carbamoyl chloride derivative by treatment with about 0.5 to 1, preferably about 0.75 equivalents of trichloromethyl chloroformate in ethyl acetate at room temperature for a period of about 2 to 3, preferably 2, hours. The resulting carbamoyl chloride derivative is then quenched with about a five fold excess of an appropriate alcohol of the formula HOAR (in which A and R have the definitions given herein), and a base such as pyridine or triethylamine. The product of Formula (6) is isolated by conventional means. Base hydrolysis of the compound of Formula (6) is then carried out in about a 1:1 mixture of aqueous sodium hydroxide and 1,2-dimethoxyethane to give the carboxylic acid of Formula (I-D).

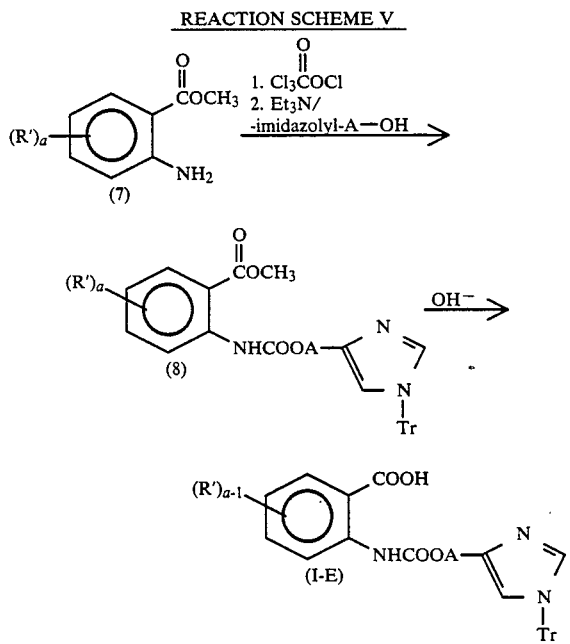

REACTION SCHEME V

Tr = Trityl radical (Triphenylmethyl radical: Ph₃C—)

A = alkylene (e.g., methylene: —CH₂—)

As shown in Reaction Scheme V, the compounds of Formula (8) are prepared from the corresponding methyl anthranilate derivative of Formula (7), disclosed as Formula (V) in U.S. patent application Ser. No. 748,631. Methyl anthranilate, as well as variously substituted methyl 2-amino benzoates (methyl anthranilates) are commercially available, or can be prepared by treating the corresponding anthranilic acid with diazomethane in an inert organic solvent such as tetrahydrofuran or preferably ether at about 0° C., a method that is standard for the formation of methyl esters. Alternatively, variously substituted methyl 2-amino benzoates can be prepared by treating the corresponding isatoic anhydride with methanol in the presence of base such as sodium methoxide or dimethylaminopyridine, preferably dimethylaminopyridine, according to the literature methods such as that reported by M. C. Venuti, *Synthesis*, 266 (1982), R. P. Straiger and E. B. Miller, *J. Org. Chem.*, 24, 1214 (1959).

The corresponding unsubstituted or appropriately substituted anthranilate of Formula (7) is treated with about 0.5 to about 1 equivalent of trichloromethyl chloroformate in tetrahydrofuran at room temperature for a period of about 1 to 2, preferably about 1.5 hours; the resulting carbamyl chloride derivative is then refluxed with about 1 to 2 equivalents of 4(N-triphenylmethyl)imidazolylmethanol, or another appropriate imidazolyl alcohol, in the presence of 5 to 10 equivalents of a tertiary amine, preferably triethylamine, for a period of about 0.5 to 2 hours. The product, a compound of Formula (8), is isolated by conventional means. The compound of Formula (I-E) is obtained by base hydrolysis of the compound of Formula (8) to the corresponding carboxylic acid.

The following examples are intended to illustrate the invention, and should not be construed as narrowing or limiting its scope. Rather, the scope of the invention is to be construed by the appended claims, including all equivalents thereto.

PREPARATIONS AND EXAMPLES

PREPARATION I

Preparation of 2-Amino-6-ethylbenzoic Acid and Related Compounds of Formula (a)

A. 2-Amino-6-ethylbenzoic acid was prepared according to Baker's procedure, as described in J. Org. Chem. 17 141(1952) and further detailed below.

(i) Preparation of m-ethyl-alpha-isonitrosoacetanilide

In a 5 liter round-bottom flask equipped with overhead stirrer and condensers were placed 74.2 g of chloral dihydrate and 900 ml of water. To this solution was then added, sequentially, 107.2 gm of anhydrous sodium sulfate, a solution of 50 gm of m-ethyl aniline dissolved in 248 ml of water and 42 ml of concentrated hydrochloric acid, and lastly, a solution of 90.8 gm of hydroxylamine hydrochloride in 412 ml of water. The mixture was slowly heated over a period of 45 minutes to a temperature of 95° C. The heating mantle was then removed and the flask rapidly cooled to room temperature by immersion in an ice-bath. The crude isonitrosoacetanilide was collected by suction filtration and washed with water. The product was then further purified by the following procedure: The crude isonitrosoacetanilide was dissolved in 500 ml of a 4 M sodium hydroxide solution, transferred to a separatory funnel and washed with ether (3×300 ml). The alkaline phase was then treated with charcoal, filtered through Celite and strongly acidified with concentrated hydrochloric acid. The precipitated m-ethyl-alpha-isonitrosoacetanilide was collected by filtration and dried under vacuum, mp. 140°-142° C.

(ii) Preparation of 4-ethyl and 6-ethyl isatin

A 1-liter round-bottom flask containing 370 ml of concentrated sulfuric acid and 30 ml of water was heated to 60° C.

m-Ethyl-alpha-isonitrosoacetanilide (64 gm) was added at such a rate as to maintain the temperature between 60° and 65° C. After the addition was completed, the mixture was heated to 80° C. for 10 minutes. The flask was then cooled to room temperature and poured onto 8 to 10 times its volume of ice. After standing for one-half hour, the crude isatin mixture was collected by filtration and washed well with water. The crude extract was then dissolved in about 300 ml of a 3M sodium hydroxide solution by heating on a steam bath, treated with charcoal and filtered through Celite. On acidification to pH 6-7 with concentrated hydrochloric acid, a gummy material appeared and was removed by filtration through Celite. The solution was then acidified to pH 4 and the 4-ethyl isatin was collected by filtration and washed with water: Yield 14.6 gm, mp. 128°–136° C. The cooled filtrate was then strongly acidified with concentrated hydrochloric acid and collected by filtration to give the 6-ethyl isatin: Yield 16.4 gm (28%), mp. 171°–173° C.

(iii) Preparation of 4-ethyl-2-amino-benzoic acid

In a 500 ml flask, was placed 16.84 gm of 6-ethyl isatin which was covered with 216 ml of 1.5 M sodium hydroxide solution. With stirring, the mixture was warmed to 50° C. Heating was discontinued and the solution was treated with a 30% solution of hydrogen peroxide (24 ml) which was added at such a rate to maintain the temperature at between 50° to 65° C.

The mixture was left to slowly cool to room temperature and was then acidified to pH 4 with concentrated hydrochloric acid. The precipitated product was then collected by filtration: mp. 117°–120° C.; yield 8.93 g.

(iv) Preparation of 6-ethyl-2-amino-benzoic acid

Oxidation of 9.6 gm of 4-ethyl isatin according to the method described in (iii), above, gave 7.3 gm of the title compound: mp. 99°–104° C.

B. By following the procedure of Part A, but replacing m-ethylaniline with the appropriate m-alkylaniline, the following exemplary compounds of Formula (a) are prepared:
2-amino-6-isopropylbenzoic acid;
2-amino-6-n-propylbenzoic acid;
2-amino-6-isobutylbenzoic acid;
2-amino-6-sec-butylbenzoic acid;
2-amino-6-n-butylbenzoic acid;
2-amino-6-t-butylbenzoic acid;
2-amino-6-n-pentylbenzoic acid; and
2-amino-6-n-hexylbenzoic acid.

PREPARATION II

Preparation of N-Butyl Chloroformate and Related Compounds of Formula (b)

A. Phosgene was passed into dry ether until saturated (15–20% w/v). N-Butyl alcohol (10 gm) in dry ether (50 ml) was treated with the ethereal phosgene (1.1 mol.) at room temperature until the reaction was complete. Removal of the solvent in vacuo gave n-butyl chloroformate in quantitative yield. In representative cases these compounds were purified by distillation, but this is not necessary for the subsequent cyclization. For the preparation of the chloroformates of hindered alcohols, quinoline can be added as a catalyst, quinoline hydrochloride being subsequently removed by filtration.

B. By following the procedure of Part A, but replacing the n-butyl alcohol with methanol, ethanol, isopropyl alcohol, n-propyl alcohol, isobutyl alcohol, tert-butyl alcohol, n-butyl alcohol, s-butyl alcohol, n-pentyl alcohol, n-hexyl alcohol, phenol or benzyl alcohol, respectively, the following compounds of Formula (b) are prepared:
methyl chloroformate;
ethyl chloroformate;
isopropyl chloroformate;
n-propyl chloroformate;
isobutyl chloroformate;
t-butyl chloroformate;
n-butyl chloroformate;
s-butyl chloroformate;
n-pentyl chloroformate;
n-hexyl chloroformate;
phenyl chloroformate; and
benzyl chloroformate.

PREPARATION III

Preparation of 2-Ethoxy-5-methyl-4H-3,1-benzoxazin-4-one and Related Compounds of Formula (1)

A. To a solution of 2-amino-6-methyl benzoic acid (25g., 0.165 mol) in dry pyridine (125 ml) at room temperature under anhydrous conditions was added ethyl chloroformate (47.33 ml, 3 equiv.) in a dropwise manner over 15 minutes. After stirring for 2 hours, the excess pyridine was removed under reduced pressure at a bath temperature of 40° C., and the residue was stirred vigorously in ice-cold water (250 ml) for 15 minutes. The pale yellow powder was collected by filtration, washed with water (100 ml) and air-dried to give the crude product (30.4g). The crude product was treated with active charcoal (2g) in ether (200ml) to afford a white solid after removal of solvent. Recrystallization from EtOAc/pet. ether gave 2-ethoxy-5-methyl-4H-3,1-benzoxazin-4-one (28.1g, 83%) as colorless crystals; m.p. 104°–105° C.; analysis for $C_{11}H_{11}NO_3$: C, 64.38; H, 5.40; N, 6.83. Found: C, 64.21; H, 5.43; N, 6.80.

B. By following the procedure of Part A, but replacing 2-amino-6-methyl benzoic acid with the appropriate aminobenzoic acid prepared in Preparation I, and/or replacing ethyl chloroformate with the appropriate chloroformate prepared in Preparation II, the following compounds of Formula (1) are prepared:
2-methoxy-5-ethyl-4H-3,1-benzoxazin-4-one;
2-methoxy-5-isopropyl-4H-3,1-benzoxazin-4-one;
2-methoxy-5-n-propyl-4H-3,1-benzoxazin-4-one;
2-methoxy-5-isobutyl-4H-3,1-benzoxazin-4-one;
2-methoxy-5-sec-butyl-4H-3,1-benzoxazin-4-one;
2-methoxy-5-n-butyl-4H-3,1-benzoxazin-4-one;
2-methoxy-5-tert-butyl-4H-3,1-benzoxazin-4-one;
2-methoxy-5-n-pentyl-4H-3,1-benzoxazin-4-one;
2-methoxy-5-n-hexyl-4H-3,1-benzoxazin-4-one;
2-ethoxy-5-ethyl-4H-3,1-benzoxazin-4-one;
2-ethoxy-5-isopropyl-4H-3,1-benzoxazin-4-one;
2-ethoxy-5-n-propyl-4H-3,1-benzoxazin-4-one;
2-ethoxy-5-isobutyl-4H-3,1-benzoxazin-4-one;
2-ethoxy-5-sec-butyl-4H-3,1-benzoxazin-4-one;
2-ethoxy-5-n-butyl-4H-3,1-benzoxazin-4-one;
2-ethoxy-5-tert-butyl-4H-3,1-benzoxazin-4-one;
2-ethoxy-5-n-pentyl-4H-3,1-benzoxazin-4-one;
2-ethoxy-5-n-hexyl-4H-3,1-benzoxazin-4-one;
2-propoxy-5-ethyl-4H-3,1-benzoxazin-4-one;
2-propoxy-5-isopropyl-4H-3,1-benzoxazin-4-one;
2-propoxy-5-n-propyl-4H-3,1-benzoxazin-4-one;
2-propoxy-5-isobutyl-4H-3,1-benzoxazin-4-one;
2-propoxy-5-sec-butyl-4H-3,1-benzoxazin-4-one;
2-propoxy-5-n-butyl-4H-3,1-benzoxazin-4-one;
2-propoxy-5-tert-butyl-4H-3,1-benzoxazin-4-one;
2-propoxy-5-n-pentyl-4H-3,1-benzoxazin-4-one;
2-propoxy-5-n-hexyl-4H-3,1-benzoxazin-4-one;
2-butoxy-5-ethyl-4H-3,1-benzoxazin-4-one;
2-butoxy-5-isopropyl-4H-3,1-benzoxazin-4-one;
2-butoxy-5-n-propyl-4H-3,1-benzoxazin-4-one;
2-butoxy-5-isobutyl-4H-3,1-benzoxazin-4-one;
2-butoxy-5-sec-butyl-4H-3,1-benzoxazin-4-one;
2-butoxy-5-n-butyl-4H-3,1-benzoxazin-4-one;
2-butoxy-5-tert-butyl-4H-3,1-benzoxazin-4-one;
2-butoxy-5-n-pentyl-4H-3,1-benzoxazin-4-one;
2-butoxy-5-n-hexyl-4H-3,1-benzoxazin-4-one;

2-pentoxy-5-ethyl-4H-3,1-benzoxazin-4-one;
2-pentoxy-5-isopropyl-4H-3,1-benzoxazin-4-one;
2-pentoxy-5-n-propyl-4H-3,1-benzoxazin-4-one;
2-pentoxy-5-isobutyl-4H-3,1-benzoxazin-4-one;
2-pentoxy-5-sec-butyl-4H-3,1-benzoxazin-4-one;
2-pentoxy-5-n-butyl-4H-3,1-benzoxazin-4-one;
2-pentoxy-5-tert-butyl-4H-3,1-benzoxazin-4-one;
2-pentoxy-5-n-pentyl-4H-3,1-benzoxazin-4-one;
2-pentoxy-5-n-hexyl-4H-3,1-benzoxazin-4-one;
2-phenoxy-5-ethyl-4H-3,1-benzoxazin-4-one;
2-phenoxy-5-isopropyl-4H-3,1-benzoxazin-4-one;
2-phenoxy-5-n-propyl-4H-3,1-benzoxazin-4-one;
2-phenoxy-5-isobutyl-4H-3,1-benzoxazin-4-one;
2-phenoxy-5-sec-butyl-4H-3,1-benzoxazin-4-one;
2-phenoxy-5-n-butyl-4H-3,1-benzoxazin-4-one;
2-phenoxy-5-tert-butyl-4H-3,1-benzoxazin-4-one;
2-phenoxy-5-n-pentyl-4H-3,1-benzoxazin-4-one;
2-phenoxy-5-n-hexyl-4H-3,1-benzoxazin-4-one;
2-benzyloxy-5-ethyl-4H-3,1-benzoxazin-4-one;
2-benzyloxy-5-isopropyl-4H-3,1-benzoxazin-4-one;
2-benzyloxy-5-n-propyl-4H-3,1-benzoxazin-4-one;
2-benzyloxy-5-isobutyl-4H-3,1-benzoxazin-4-one;
2-benzyloxy-5-sec-butyl-4H-3,1-benzoxazin-4-one;
2-benzyloxy-5-n-butyl-4H-3,1-benzoxazin-4-one;
2-benzyloxy-5-tert-butyl-4H-3,1-benzoxazin-4-one;
2-benzyloxy-5-n-pentyl-4H-3,1-benzoxazin-4-one;
2-benzyloxy-5-n-hexyl-4H-3,1-benzoxazin-4-one;
2-(4-ethyiphenoxy)-5-ethyl-4H-3,1-benzoxazin-4-one;
2-(3-chlorophenoxy)-5-ethyl-4H-3,1-benzoxazin-4-one;
2-(4-methoxyphenoxy)-5-ethyl-4H-3,1-benzoxazin-4-one;
2-(4-methylthiophenoxy)-5-ethyl-4H-3,1 -benzoxazin-4-one;
2-(4-nitrophenoxy)-5-methyl-4H-3,1-benzoxazin-4-one;
2-cyclohexyloxy-5-ethyl-4H-3,1-benzoxazin-4-one;
2-(2-methylcyclohexyl)-5-ethyl-4H-3,1 -benzoxazin-4-one;
2-cyclopentoxy-5-ethyl-4H-3,1-benzoxazin-4-one;
2-(2-chlorocyclohexyloxy)-5-ethyl-4H-3,1-benzoxazin-4-one;
2-cyclobutyloxy-5-ethyl-4H-3,1-benzoxazin-4-one;
2-ethoxy-7-nitro-4H-3,1-benzoxazin-4-one;
2-ethoxy-7-amino-4H-3,1-benzoxazin-4-one;
2-ethoxy-7-ethoxycarbonylamino-4H-3,1-benzoxazin-4-one;
2-ethoxy-6-chloro-4H-3,1-benzoxazin-4-one;
2-ethoxy-6-methyl-4H-3,1-benzoxazin-4-one;
2-ethoxy-6-benzyl-4H-3,1-benzoxazin-4-one;
2-ethoxy-7-ethyl-4H-3,1-benzoxazin-4-one;
2-ethoxy-7-methoxy-4H-3,1-benzoxazin-4 -one;
2-ethoxy-7-methylthio-4H-3,1-benzoxazin-4-one;
2-ethoxy-7-hydroxy-4H-3,1-benzoxazin-4-one;
2-ethoxy-7-nitro-5-ethyl-4H-3,1-benzoxazin-4-one;
2-ethoxy-7-(3,3-dimethylureido)-4H-3,1-benzoxazin-4-one; and
2-ethoxy-7-methoxy-5-methyl-4H-3,1-benzoxazin-4-one.

PREPARATION IV

Preparation of Ethyl 2-Ethoxycarbonylamino-6-methylbenzoate and Related Compounds of Formula (2)

To a solution of 2-ethoxycarbonylamino-5-methyl-4H-3,1-benzoxazin-4-one (25 g 0.122 mol.) in absolute ethanol (100 ml) at 0° C. was added a solution of freshly prepared 1M sodium ethoxide solution until pH 8.5 was attained. After stirring at 0° C. (pH 8.5) for two hours, the reaction mixture was poured into 400 ml of ice-cold water with vigorous stirring. The pale yellow benzoate of Formula (5) was collected by filtration and air-dried. The yield was quantitative. Further recrystallization from pentane gave white crystals; mp 38.5°–39.5° C.

PREPARATION V

Preparation of Ethyl 2-Ethoxycarbonylamino-6-bromomethylbenzoate and Related Compounds of Formula (3)

A solution of ethyl 2-ethoxycarbonylamino-6-methylbenzoate (10 mmol, 2.513 g.), N-bromosuccinimide (11 mmol, 1.957 g.), and catalytic amount (100 mg) of AIBN (2,2'-azobisisobutyronitrile) in 50 ml carbon tetrachloride was refluxed for 2 hours. The insoluble succinimide was removed by filtration. The filtrate was washed with saturated $NaHCO_3$ solution (25 ml), water (30 ml), dried over $MgSO_4$, and filtered. The filtrate was evaporated to dryness and trituated with petroleum ether to afford 2.44 g (74%) of ethyl 2-ethoxycarbonylamino-6-bromomethylbenzoate (6) as a pale yellow powder; mp 70°–72° C. IR (KBr) $\nu_{max}$ 1740, 1685 $cm^{-1}$.

H-NMR ($CDCl_3$): δ1.31 ppm (t, J=7.2 ppm, 3H), 1.57 ppm (t, J=7.2 ppm, 3H), 4.21 ppm (q, J=7.2 ppm, 2H), 4.50 ppm (q, J=7.2 ppm, 2H), 4.75 ppm (S, 2H), 7.0–8.3 ppm (m, 3H), and 9.05 ppm (b, 1H).

PREPARATION VI

Preparation of the Phosphonium Salt of Formula (4)

A solution of ethyl 2-ethoxycarbonylamino-6-bromomethylbenzoate (2 mmol 660 mg) and triphenylphosphine (2.4 mmol 629 mg) in dry THF (10 ml) was refluxed for 4 hours under anhydrous conditions in a three neck flask. The expected phosphonium salt (4) was precipitated out of the solution. The mixture was cooled in ice, diluted with 20 ml diethyl ether, and the supernatant was decanted under positive $N_2$ pressure through a side arm adaptor leaving the phosphonium salt (4) (white powder) in the flask.

PREPARATION VII

Preparation of Methyl 4,5-dimethoxy-2-[4-(N-triphenylmethyl)imidazolyl]-methoxycarbonylamino Benzoate and Related Compounds of Formula (8)

A. Trichloromethyl chloroformate (0.16 ml, 1.2 mmol.) was added to a solution of methyl 4,5-dimethoxy-2-aminobenzoate (422 mg, 2 mmol.) in dry THF (30 ml) at room temperature under argon. After stirring for 90 minutes, anhydrous triethylamine (2 ml, 14.4 mmol.) and 4(N-triphenylmethyl)imidazolymethanol (749 mg, 2.2 mmol.) were added and the mixture was refluxed for one hour. The solvent was removed under reduced pressure. The residue was shaken with a mixture of ether/water (40 ml/40 ml) and the insoluble solid was collected by filtration to afford 936 mg (81%) of methyl 4,5-dimethoxy-2-[4-(N-triphenylmethyl)imidazolyl)methoxycarbonylamino benzoate as a fine powder; m.p. 190°–192° C.;

IR (KBr):$\nu_{max}$ 3267 $cm^{-1}$ (NH), 1730 $cm^{-1}$ (carbamate), 1690 ($COOCH_3$); H'NMR ($CDCl_3$): δ3.88 ppm (s, 6H, $OCH_3$), 5.13 ppm (s, 2H, $OCH_2$), 6.95–7.44 ppm (m, 18H, aromatic protons and imidazolyl C -H), 8.16 (s, 1H, imidazolyl $C_2$-$\underline{H}$). 10.49 ppm (s, 1H, N$\underline{H}$).

B. In a like manner, but starting instead with other appropriately substituted benzoates, the following representative compounds of Formula (8) are obtained:

methyl 6-methyl-2-[4-(N-triphenylmethyl)imidazolyl]methoxycarbonylamino benzoate;
methyl 6-ethyl-2-[4-(N-triphenylmethyl)imidazolyl]methoxycarbonylamino benzoate;
methyl 6-chloro-4-nitro-2-[4-(N-triphenylmethyl)imidazolyl]methoxycarbonylamino benzoate;
methyl 6-ethylthio-4-bromomethyl-2-[4-(N-triphenylmethyl)imidazolyl]methoxycarbonylamino benzoate;
methyl 4-amino-6-ethyl-2-[4-(N-triphenylmethyl)imidazolyl]methoxycarbonylamino benzoate, and
methyl 4-amino-6-methyl-2-[4-(N-triphenylmethyl)imidazolyl]methoxycarbonylamino benzoate.

EXAMPLE I

Preparation of 2-Ethoxycarbonylamino-6-methylbenzoic Acid and Related Compounds of Formula I By Reaction Scheme I A. 2-Ethoxy-5-methyl-4H-3,1-benzoxazin-4-one (20 g., 97.56 mmol) of Preparation III herein, and 4N HCl (10 ml), were stirred in tetrahydrofuran (THF, 200 ml) at room temperature for 15 minutes. The reaction mixture was evaporated to dryness under reduced pressure. The residue was dissolved in ethyl acetate (250 ml), washed with water (3×150 ml), and evaporated to give a pale yellow solid. Recrystallization from ethyl acetate/ pet. ether afforded 2-ethoxycarbonylamino-6-methylbenzoic acid (16.18 g, 74%) as colorless crystals; m.p. 123.5°–125° C.; analysis for $C_{11}H_{13}NO_4$: C, 59.19; H, 5.87; N, 6.27. Found: C, 59.32; H, 5.95; N, 6.25.

B. By following the procedure of Part A, but replacing 2-ethoxy-5-methyl-4H-3,1-benzoxazin-4-one with the appropriate benzoxazinone prepared in Preparation III, the following compounds of Formula I are prepared:

2-methoxycarbonylamino-6-ethylbenzoic acid;
2-methoxycarbonylamino-6-isopropylbenzoic acid;
2-methoxycarbonylamino-6-n-propylbenzoic acid;
2-methoxycarbonylamino-6-isobutylbenzoic acid;
2-methoxycarbonylamino-6-n-butylbenzoic acid;
2-methoxycarbonylamino-6-tert-butylbenzoic acid;
2-methoxycarbonylamino-6-n-pentylbenzoic acid;
2-methoxycarbonylamino-6-n-hexylbenzoic acid;
2-ethoxycarbonylamino-6-ethylbenzoic acid;
2-ethoxycarbonylamino-6-isopropylbenzoic acid;
2-ethoxycarbonylamino-6-n-propylbenzoic acid;
2-ethoxycarbonylamino-6-isobutylbenzoic acid;
2-ethoxycarbonylamino-6-n-butylbenzoic acid;
2-ethoxycarbonylamino-6-tert-butylbenzoic acid;
2-ethoxycarbonylamino-6-n-pentylbenzoic acid;
2-ethoxycarbonylamino-6-n-hexylbenzoic acid;
2-propoxycarbonylamino-6-ethylbenzoic acid;
2-propoxycarbonylamino-6-isopropylbenzoic acid;
2-propoxycarbonylamino-6-n-propylbenzoic acid;
2-propoxycarbonylamino-6-isobutylbenzoic acid;
2-propoxycarbonylamino-6-n-butylbenzoic acid;
2-propoxycarbonylamino-6-tert-butylbenzoic acid;
2-propoxycarbonylamino-6-n-pentylbenzoic acid;
2-propoxycarbonylamino-6-n-hexylbenzoic acid;
2-butoxycarbonylamino-6-ethylbenzoic acid;
2-butoxycarbonylamino-6-isopropylbenzoic acid;
2-butoxycarbonylamino-6-n-propylbenzoic acid;
2-butoxycarbonylamino-6-isobutylbenzoic acid;
2-butoxycarbonylamino-6-n-butylbenzoic acid;
2-butoxycarbonylamino-6-tert-butylbenzoic acid;
2-butoxycarbonylamino-6-n-pentylbenzoic acid;
2-butoxycarbonylamino-6-n-hexylbenzoic acid;
2-pentoxycarbonylamino-6-ethylbenzoic acid;
2-pentoxycarbonylamino-6-isopropylbenzoic acid;
2-pentoxycarbonylamino-6-n-propylbenzoic acid;
2-pentoxycarbonylamino-6-isobutylbenzoic acid;
2-pentoxycarbonylamino-6-n-butylbenzoic acid;
2-pentoxycarbonylamino-6-tert-butylbenzoic acid;
2-pentoxycarbonylamino-6-n-pentylbenzoic acid;
2-pentoxycarbonylamino-6-n-hexylbenzoic acid;
2-phenoxycarbonylamino-6-ethylbenzoic acid;
2-phenoxycarbonylamino-6-isopropylbenzoic acid;
2-phenoxycarbonylamino-6-n-propylbenzoic acid;
2-phenoxycarbonylamino-6-isobutylbenzoic acid;
2-phenoxycarbonylamino-6-n-butylbenzoic acid;
2-phenoxycarbonylamino-6-tert-butylbenzoic acid;
2-phenoxycarbonylamino-6-n-pentylbenzoic acid;
2-phenoxycarbonylamino-6-n-hexylbenzoic acid;
2-benzyloxycarbonylamino-6-ethylbenzoic acid;
2-benzyloxycarbonylamino-6-isopropylbenzoic acid;
2-benzyloxycarbonylamino-6-n-propylbenzoic acid;
2-benzyloxycarbonylamino-6-isobutylbenzoic acid;
2-benzyloxycarbonylamino-6-n-butylbenzoic acid;
2-benzyloxycarbonylamino-6-tert-butylbenzoic acid;
2-benzyloxycarbonylamino-6-n-pentylbenzoic acid; and
2-benzyloxycarbonylamino-6-n-hexylbenzoic acid;
2-(4-ethylphenoxy)carbonylamino-6-ethylbenzoic acid;
2-(3-chlorophenoxy)carbonylamino-6-ethylbenzoic acid;
2-(4-methoxyphenoxy)carbonylamino-6-ethylbenzoic acid;
2-(4-methylthiophenoxy)carbonylamino-6-ethylbenzoic acid;
2-(4-nitrophenoxy)carbonylamino-6-methylbenzoic acid;
2-cyclohexyloxycarbonylamino-6-ethylbenzoic acid;
2-(2-methylcyclohexyl)carbonylamino-6-ethylbenzoic acid;
2-cyclopentoxycarbonylamino-6-ethylbenzoic acid;
2-(2-chlorocyclohexyloxy)carbonylamino-6-ethylbenzoic acid;
2-cyclobutyloxycarbonylamino-6-ethylbenzoic acid;
2-ethoxycarbonylamino-4-nitrobenzoic acid;
2-ethoxycarbonylamino-4-aminobenzoic acid;
2-ethoxycarbonylamino-4-ethoxycarbonylaminobenzoic acid;
2-ethoxycarbonylamino-5-chlorobenzoic acid;
2-ethoxycarbonylamino-5-methylbenzoic acid;
2-ethoxycarbonylamino-5-benzylbenzoic acid;
2-ethoxycarbonylamino-4-ethoxybenzoic acid;
2-ethoxycarbonylamino-4-methoxybenzoic acid;
2-ethoxycarbonylamino-5-methylthiobenzoic acid;
2-ethoxycarbonylamino-4-hydroxybenzoic acid;
2-ethoxycarbonylamino-4-nitro-6-ethylbenzoic acid;
2-ethoxycarbonylamino-4-(3,3-dimethylureidobenzoic acid; and
2-ethoxycarbonylamino-4-methoxy-6-methylbenzoic acid.

EXAMPLE II

Preparation of 2-Ethoxycarbonylamino-6-vinylbenzoic acid and Related Compounds of Formula (I-B$^1$) By Reaction Scheme II To phosphonium salt (4) and paraformaldehyde (5 equiv. $(CH_2O)_n$, 300 mg) in 10 ml anhydrous ether was added solid Potassium t-butoxide (Aldrich) (2.2 mmol, 246 mg) at 0° C. under anhydrous conditions. The bright yellow color of the solution slowly fades. Stirring was continued for an hour at 0° C. The supernatant of the reaction mixture was decanted and the residue was washed twice with ice-cold ether (2×10 ml). The combined supernatant and etherate solution was washed with 1N HCl (10 ml), water (2×10 ml), dried (MgSO₄), filtered, and evaporated to dryness. The residue was then stirred in 20 ml aqueous NaOH (pH 10) at room temperature overnight. After the hydrolysis was completed, the aqueous reaction mixture was extracted with toluene (2×10 ml) to remove trace amounts of triphenylphosphine oxide. The aqueous layer was then acidified to pH 3 with 1N HCl and the product was extracted into ether (40 ml). The etherate solution was washed with water (2×25 ml), dried with MgSO₄, filtered, and evaporated to dryness. Recrystallization from ether-pentane gave 2-ethoxycarbonylamino-6-vinylbenzoic acid as white crystals (111 mg, 21%). M.p. 71.5-74.0; IR (KBr) $\nu_{max}$=1725, 1700 cm$^{-1}$.

H-NMR (CDCl₃): $\delta$1.35 ppm (t, J=7.2 Hz, 3H), 4.30 ppm (q, J=7.2 Hz, 2H), 5.38 ppm (dd, $J_1$=10.8 Hz, $J_2$=1.3 Hz, 1H), 6.68 ppm (dd, $J_1$=17.3 Hz, $J_2$1.3 Hz, 1H), 7.05-8.3 ppm (m, 4H), 9.10 (b, 1H).

In a similar manner, but replacing the paraformadehyde with acetaldehyde and propionaldehyde, the compounds of Formula (I-B$^1$) where R" is methyl or ethyl, are prepared.

EXAMPLE III

Preparation of 2-Ethoxycarbonylamino-6-ethylbenzoic Acid and Related Compounds of Formula (I-B²) By Reaction Scheme II A. 2-Ethoxycarbonylamino-6-vinyl benzoic acid (500 mg, 2.13 mmol) and 10% Pd-C (50 mg) in 40 ml absolute ethanol was stirred for 16 hrs under 40 psi H₂ pressure in a Parr bomb at room temperature. The reaction mixture was filtered through a cone of Celite and the catalyst on Celite was washed with 15 ml ethanol. The combined filtrate was evaporated to dryness. Trituration with ether gave crystalline 2-ethoxycarbonylamino-6-ethylbenzoic acid of Formula (I) in quantitative yield. M.p. 71.5°-74.0° C.; IR (KBr) $\nu_{max}$=1725, 1700 cm$^{-1}$. Analysis, C₁₂H₁₅NO₄: theory, C 60.75; H 6.37; H 5.90; found, C 60.82; H 6.38; N 5.88.

H-NMR (CDCl₃): 1.25 ppm (t, J=7.5 Hz, 3H), 1.32 ppm (t, J=7.12 Hz, 3H), 2.90 ppm (q, J=7.5 Hz, 2H), 4.25 ppm (q, J=7.12 Hz, 2H), 6.64-8.05 ppm (m, 3H), 8.78 ppm (b, 1H).

B. By following the procedure of Part A, the following compounds were prepared:
2-ethoxycarbonylamino-6-n-propylbenzoic acid, m.p. 94°-98° C., and
2-ethoxycarbonylamino-6-n-butylbenzoic acid, m.p. 69° C.

EXAMPLE IV

Preparation of 2-ethoxycarbonylamino-6-propenylbenzoic Acid and Related Compounds of Formula (I-C$^1$) by Reaction Scheme III A solution of 2-ethoxy-5-propenyl-4H-3,1-benzoxazin-4-one (Example X, page 65, U.S. patent application Ser. No. 748,631) in DME (10 ml) and 0.5% sulphuric acid (10 ml) was stirred at room temperature for 45 minutes. The solution was extracted with ethyl acetate.

The ethyl acetate layer was dried over MgSO₄ and evaporated to an oil.

Alternatively, the title compound was prepared by stirring a solution of 2-ethoxy-5-propenyl-4H-3,1-benzoxazin-4-one in THF (5 ml) and 2% sodium hydroxide (5 ml) for 6 hours. The organic solvent was removed by evaporation. The aqueous solution was acidified to pH=2 with dropwise addition of 6 M HCl. The solution was extracted with ethyl acetate and the organic was dried (magnesium sulphate) and evaporated to give an oil.

IR $\nu_{max}$=1680-1740, 160 cm$^{-1}$, 2500-3200 (br).

EXAMPLE V

Preparation of 2-ethoxycarbonylamino-6-propylbenzoic Acid and Related Compounds of Formula (I-C²) by Reaction Scheme III A solution of 2-ethoxycarbonylamino-6-propenylbenzoic acid (220 mg) in ethanol was hydrogenated at 50 psi hydrogen over 10% palladium on charcoal. After 3 hours, the catalyst was filtered through Celite and the filtrate evaporated to give an oily solid (194 mg). IR $\nu_{max}$=1680-1740 (br), 2500-3200 (br).

EXAMPLE VI

Preparation of 2-Ethoxycarbonylamino-4-nitro-6-ethylbenzoic acid and Related Compounds of Formula (I-D) By Reation Scheme IV A. A solution of ethyl 2-ethoxycarbonylamino-4-nitro-6-ethyl-benzoate in tetrahydrofuran (10 ml) and sodium hydroxide (20 ml, 10%) was stirred at room temperature for 20 hours. The solution was extracted with ethyl acetate. The aqueous layer was acidified to pH=1 with 6M HCl, and then immediately extracted with ethylacetate. The ethyl acetate extract was washed with water and dried over magnesium sulphate. Solvent evaporation gave a solid which was further recrystallized from methylene chloride: petroleum ether to yield 2-ethoxycarbonylamino-4-nitro-6-ethyl benzoic acid, m.p. 121°-123° C. as orange crystals. IR $\nu_{max}$: 1665, 1720, 1620, 1510, 2500-3200(br), 3500cm.

B. Proceeding in a similar manner, but replacing the 2-ethoxycarbonylamino-4-nitro-6-ethyl-benzoate with other appropriately substituted benzoates described in U.S. patent application Ser. No. 748,631 as Formula VIII (Reaction Scheme IX) therein, the preparation of which are described in Preparation V therein, the following compounds of Formula (I-D) are prepared:
2-benzyloxycarbonylamino-6-ethyl-4-nitrobenzoic acid;
2-ethyloxycarbonylamino-6-methyl-4-nitrobenzoic acid;
2-isopropyloxycarbonylamino-6-propyl-4-nitrobenzoic acid;
2-isopropyloxycarbonylamino-6-butyl-4-nitrobenzoic acid; and
2-cyclopropyloxycarbonylamino-6-isobutyl-4-nitrobenzoate.

C. Other examples of compounds that can be made by Reaction Scheme II are:
2-methoxycarbonylamino-5-ethylbenzoic acid;
2-ethoxycarbonylamino-5-ethylbenzoic acid;
2-ethoxycarbonylamino-5-propylbenzoic acid;
2-ethoxycarbonylamino-5-butylbenzoic acid;
2-propoxycarbonylamino-5-ethylbenzoic acid;
2-propoxycarbonylamino-5-propylbenzoic acid;

2-propoxycarbonylamino-5-butylbenzoic acid;
2-butoxycarbonylamino-5-ethylbenzoic acid;
2-butoxycarbonylamino-5-propylbenzoic acid;
2-butoxycarbonylamino-5-butylbenzoic acid;
2-phenoxycarbonylamino-5-ethylbenzoic acid;
2-phenoxycarbonylamino-5-propylbenzoic acid;
2-phenoxycarbonylamino-5-butylbenzoic acid;
2-phenylethoxycarbonylamino-5-ethylbenzoic acid;
2-phenylethoxycarbonylamino-5-propylbenzoic acid;
2-phenylethoxycarbonylamino-5-butylbenzoic acid; and
2-phenylbutoxycarbonylamino-5-ethylbenzoic acid.

D. Similarly, compounds with an alkyl group at positions 6, 7 or 8 can be prepared by this Reaction Scheme, such as:
2-methoxycarbonylamino-6-ethylbenzoic acid;
2-ethoxycarbonylamino-6-ethylbenzoic acid;
2-ethoxycarbonylamino-6-propylbenzoic acid;
2-ethoxycarbonylamino-6-butylbenzoic acid;
2-propoxycarbonylamino-6-ethylbenzoic acid;
2-propoxycarbonylamino-6-propylbenzoic acid;
2-propoxycarbonylamino-6-butylbenzoic acid;
2-butoxycarbonylamino-6-ethylbenzoic acid;
2-butoxycarbonylamino-6-propylbenzoic acid;
2-butoxycarbonylamino-6-butylbenzoic acid;
2-phenoxycarbonylamino-6-ethylbenzoic acid;
2-phenoxycarbonylamino-6-propylbenzoic acid;
2-phenoxycarbonylamino-6-butylbenzoic acid;
2-phenylethoxycarbonylamino-6-ethylbenzoic acid;
2-phenylethoxycarbonylamino-6-propylbenzoic acid;
2-phenylethoxycarbonylamino-6-butylbenzoic acid;
2-phenylbutoxycarbonylamino-6-ethylbenzoic acid;
2-methoxycarbonylamino-7-ethylbenzoic acid;
2-ethoxycarbonylamino-7-ethylbenzoic acid;
2-ethoxycarbonylamino-7-propylbenzoic acid;
2-ethoxycarbonylamino-7-butylbenzoic acid;
2-propoxycarbonylamino-7-ethylbenzoic acid;
2-propoxycarbonylamino-7-propylbenzoic acid;
2-propoxycarbonylamino-7-butylbenzoic acid;
2-butoxycarbonylamino-7-ethylbenzoic acid;
2-butoxycarbonylamino-7-propylbenzoic acid;
2-butoxycarbonylamino-7-butylbenzoic acid;
2-phenoxycarbonylamino-7-ethylbenzoic acid;
2-phenoxycarbonylamino-7-propylbenzoic acid;
2-phenoxycarbonylamino-7-butylbenzoic acid;
2-phenylethoxycarbonylamino-7-ethylbenzoic acid;
2-phenylethoxycarbonylamino-7-propylbenzoic acid;
2-phenylethoxycarbonylamino-7-butylbenzoic acid;
2-phenylbutoxycarbonylamino-7-ethylbenzoic acid;
2-methoxycarbonylamino-8-ethylbenzoic acid;
2-ethoxycarbonylamino-8-ethylbenzoic acid;
2-ethoxycarbonylamino-8-propylbenzoic acid;
2-ethoxycarbonylamino-8-butylbenzoic acid;
2-propoxycarbonylamino-8-ethylbenzoic acid;
2-propoxycarbonylamino-8-propylbenzoic acid;
2-propoxycarbonylamino-8-butylbenzoic acid;
2-butoxycarbonylamino-8-ethylbenzoic acid;
2-butoxycarbonylamino-8-propylbenzoic acid;
2-butoxycarbonylamino-8-butylbenzoic acid;
2-phenoxycarbonylamino-8-ethylbenzoic acid;
2-phenoxycarbonylamino-8-propylbenzoic acid;
2-phenoxycarbonylamino-8-butylbenzoic acid;
2-phenylethoxycarbonylamino-8-ethylbenzoic acid;
2-phenylethoxycarbonylamino-8-propylbenzoic acid;
2-phenylethoxycarbonylamino-8-butylbenzoic acid; and
2-phenylbutoxycarbonylamino-8-ethylbenzoic acid.

EXAMPLE VII

Preparation of 4,5-dimethoxy-2-[(4-(N-triphenylmethyl)imidazolyl)-methyloxycarbonylamino] Benzoic Acid and Related Compounds of Formula (I-E) of Reaction Scheme V Methyl 4,5-dimethoxy-2-[(4-(N-triphenylmethyl)-imidazolyl)methyloxycarbonylamino] benzoic acid, prepared as described in Paragraph A of Preparation VII, was stirred in a solution of 1N NaOH (10 ml), THF (20), and methanol (20 ml) at room temperature for 3 hours. The organic solvent was removed under reduced pressure at 35° C. (bath temperature). The aqueous residue was diluted with water (15 ml) and acidified to pH 4 with 1 N HCl. The white precipitate was collected by filtration to yield 73 mg of the title compound. The acidic filtrate was saturated with sodium chloride and extracted with ethyl acetate. The organic extract was dried over magnesium sulphate and evaporated to afford 173 mg of the title compound. The combined yield of the benzoic acid was 246 mg (60%); mp. 200° C. (decomp.); IR $\nu_{max}$: 3600–2800, 1730, 1670 cm$^{-1}$.

The following compounds are also prepared by this procedure from appropriate starting materials:

6-methyl-2-[(4-(N-triphenylmethyl)-imidazolyl)methyloxycarbonylamino]benzoic acid; and 6-ethyl-2-[(4-(N-triphenylmethyl)-imidazolyl)methyloxycarbonylamino] benzoic acid.

EXAMPLE VIII

Carrageenan-induced Paw Edema in Rat

Method: Test for Determining Anti-Inflammatory Activity Utilizing Carrageenan-Induced Paw Inflammation in Rats The method used was basically that of Winter, et al. (See, Winter, C.A., Risley, E.A., and Nuss, G.W.: *Carrageenan-induced edema in hind paw of the rat as an assay for anti-inflammatory drugs*, Proc. Soc. Exp. Biol. Med. 111:544–547, 1962.) Female albino rats (Sim: (SD)fbr) weighing 80–90 g received the test material p.o. in 1 ml aqueous vehicle at hour zero (0 hr). One hour later (hr 1), 0.05 ml of a 1% solution (in aqueous 0.9% NaCl) or carrageenan was injected into the right hind paw to inflame the paw. The rats were sacrificed at hour 4, at which time both hind paws were removed and individually weighed. The percent increase in the weight of the inflamed paw over that of the opposite non-inflamed paw was calculated.

TABLE 1

Effect of Agents on Carrageenan-induced paw edema in the rat after oral administration one hour prior to Carrageenan injection.

| Agent | Oral dose, mg/kg | Inhibition of Hind Paw Weight Increase |
|---|---|---|
| Flufenamic acid | 100 | 52 |
|  | 10 | 35 |
| Dexamethasone | 0.1 | 71 |
| 2-Amino-6-methylbenzoic acid (RS-31110) | 100 | 0 |
|  | 30 | 7* |
|  | 10 | 5* |
| 2-Ethoxycarbonylamino-6-methylbenzoic acid (RS-96203) | 100 | 12* |
|  | 30 | 13* |
|  | 10 | 9* |
| 2-Isobutyloxycarbonylamino-6-methylbenzoic acid (RS-31609) | 100 | 23* |
| 2-Benzyloxycarbonylamino-6-methylbenzoic acid | 100 | 10* |

TABLE 1-continued

Effect of Agents on Carrageenan-induced paw edema in the rat after oral administration one hour prior to Carrageenan injection.

| Agent | Oral dose, mg/kg | Inhibition of Hind Paw Weight Increase |
|---|---|---|
| (RS-31251) | | |

*not significant

EXAMPLE IX

Experimental Allergic Encephalomyelitis in Rat

Method: Test for Inhibition of Experimental Allergic Encephalomyelitis Induced in Rats Female LEW/Crl BR rats weighing 125–135 g were randomly assigned to treatment groups of ten animals. Experimental allergic encephalomyelitis was induced by injecting into the right hind paw of each animal 0.1 ml of an emulsion containing 15 mg (wet weight) of syngeneic spinal cord tissue, 0.06 ml of Freund's Incomplete Adjuvant (Difco), 0.04 ml of sterile 0.9% saline and 0.2 mg of heat-killed, dried Mycobacterium butyricum (Difco). Test materials prepared as solutions or suspensions in aqueous carboxymethyl cellulose vehicle were administered orally each day for 16 days, starting on the day of injection. Animals were individually identified and weighed on day one, and again on day 17. On days 12 through 17, each animal was observed for signs of paralysis and was considered positive if hind limb flacidity was detectable on one or more days. Test materials were considered to exert a beneficial effect if less than nine animals showed signs of paralysis and/or there was significant increase in body weight for the test group in comparison to control group receiving vehicle only.

TABLE 2

Effect of Agents on Body Weights and Symptoms of Experimental Allergic Encephalomyelitis

| Agent | Dose mg/kg | Body Wt., gm | % Animals With Paralysis | |
|---|---|---|---|---|
| 2-Amino 6-methylbenzoic acid | 0 | 142 ± 2.7 | 100 | |
| | 2 | 153 ± 5.2 | 70 | |
| | 10 | 145 ± 4.1 | 90 | |
| | 50 | 141 ± 4.0 | 100 | |
| 2-Ethyloxycarbonyl amino-6-methylbenzoic acid | 0 | 138 ± 2.8 | 100 | |
| | 5 | 164 ± 4.9* | 40 | *p < 0.02 |
| | 10 | 155 ± 3.7* | 70 | |
| | 25 | 154 ± 6.0* | 80 | |
| 2-Isobutyloxycarbonyl amino-6-methylbenzoic acid | 0 | | 100 | |
| | 10 | | 70 | |
| 2-Benyloxycarbonyl- amino-6-methyl benzoic | 0 | 131 ± 0.5 | 100 | |
| | 10 | 146 ± 3.6* | 60 | *p < 0.001 |
| 2-Ethoxycarbonyl- aminobenzoic acid | 0 | 139 ± 3.4 | 100 | |
| | 2 | 150 ± 4.2 | 50 | |
| | 10 | 162 ± 3.4* | 70 | *p < 0.05 |
| | 50 | 151 ± 4.4* | 50 | |
| 2-Benzyloxycarbonyl- aminobenzoic acid | 0 | 134 ± 2.0 | 100 | |
| | 2 | 131 ± 3.6 | 100 | |
| | 10 | 141 ± 6.3 | 70 | |
| 2-Ethoxycarbonyl amino-4,5-dimethoxy- benzoic acid | 0 | 139 ± 3.4 | 100 | |
| | 2 | 157 ± 4.0* | 70 | *p < 0.05 |
| | 10 | 137 ± 5.7 | 70 | |
| | 50 | 154 ± 5.8* | 60 | |
| 2-Benzyloxycarbonyl- amino-4,5-dimethoxy- benzoic acid | 0 | 134 ± 2.0 | 100 | |
| | 2 | 142 ± 5.3 | 80 | |
| | 10 | 144 ± 3.9 | 90 | |
| Flufenamic acid | 0 | 134 ± 2.0 | 100 | |
| | 30 | 135 ± 2.4 | 100 | |
| | 100 | 128 ± 2.1 | 100 | |
| Dexamethasone | 0 | 135 ± 3.2 | 100 | |

TABLE 2-continued

Effect of Agents on Body Weights and Symptoms of Experimental Allergic Encephalomyelitis

| Agent | Dose mg/kg | Body Wt., gm | % Animals With Paralysis |
|---|---|---|---|
| | 0.25 | 130 ± 0.4 | 0 |

EXAMPLE X

Adjuvant-induced Arthritis in Rat

Method: Test for Activity in the Rat Adjuvant-Induced Arthritis Assay

Female Hla:(SD) BR rats weighing 160–180 g were randomly distributed to treatment groups of 12 animals, and were given food and water ad libitum. Test materials were prepared fresh weekly as suspensions in aqueous carboxymethyl cellulose. Animals were orally dosed with volumes of 1 ml twice per day Monday through Friday, and with 2 ml once per day on Saturdays and Sundays. At time 0, rats were injected intradermally in the proximal quarter of the tail with 0.1 ml of a mineral oil supsension of heat killed and dried Mycobacterium butyricum (Difco) at a concentration of 10 mg/ml. On day 18 immediately prior to autopsy, the intensity of swelling in the four paws and tail was estimated visually and scored (0 to 4 for paws, 0 to 3 for tail). Total maximum score, indicating intense swelling of all four paws and tail, is 19. After sacrifice, the hind paws of each animal were removed and weighed.

Method: Test for Ability to Cause Gastro-Intestinal Erosion in Rats

Male Lai: COX (SD) rats weighing 200–250 g were acclimated for one week under standard laboratory conditions. Each animal was individually identified and body weights were determined on the first day of the test and again at autopsy. The test materials, suspended in aqueous carboxymethyl cellulose vehicle, were administered orally once daily in a volume of 1.0 ml per 100 g body weight for seven consecutive days. Food was withdrawn from the animals following the last dose and the animals were sacrificed 24 hours later. At necropsy, the stomach and intestines were removed and observed for lesions. A group of five rats was used for each dose level of test material, and erosions were graded on a 1–10 scale with a score of 10 indicating that the animal died of ulceration prior to autopsy. The highest test dose level producing no detectable lesions is reported.

TABLE 3

Effect of Agents on Hind Paw Weights when administered orally to rats with Adjuvant-induced Arthritis and Ability to Induce Gastro-intestinal Ulcers.

| Agent | Inibition of Adjuvant Arthritis | Minimum Dose causing G.I. Erosions |
|---|---|---|
| Flufenamic Acid | 80% at 35 mg/kg | 35 mg/kg/day |
| 2-Amino 6-methylbenzoic acid | 0% at 50 mg/kg 30%(n.s.) | >250 mg/kg/day |
| 2-Ethyloxycarbonyl- 6-methylbenzoic acid | at 50 mg/kg | >100 mg/kg/day |
| 2-Isobutyloxycarbonyl- 6-methylbenzoic acid | 0% at 50 mg/kg | >100 mg/kg/day |
| 2-Ethoxycarbonylamino- 4,5-dimethoxy benzoic acid | 0% at 50 mg/kg | >100 mg/kg/day |

EXAMPLE XI

An injectable preparation buffered to a pH of 7 is prepared having the following composition:

| Ingredients | |
|---|---|
| Active ingredient | 0.2 g |
| $KH_2PO_4$ buffer (0.4 M solution) | 2 ml |
| KOH (1 N) | q.s. to pH 7 |
| water (distilled, sterile) | q.s. to 20 ml |

EXAMPLE XII

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.05 mg |
| distilled water | q.s. to 100 ml |

EXAMPLE XIII

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE XIV

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE XV

| Ingredients | Quantity per tablet, mgs. |
|---|---|
| Active ingredients | 200 |
| cornstarch | 50 |
| lactose | 145 |
| magnesium stearate | 5 |

The above ingredients are mixed intimately and pressed into single scored tablets.

EXAMPLE XVI

| Ingredients | Quantity per tablet, mgs. |
|---|---|
| Active ingredients | 108 |
| lactose | 15 |
| cornstarch | 25 |
| magnesium stearate | 2 |

The above ingredients are mixed and introduced into a hard-shell gelatin capsule.

EXAMPLE XVII

| Ingredients | Quantity per tablet, mgs. |
|---|---|
| Active ingredients | 150 |
| lactose | 92 |

The above ingredients are mixed and introduced into a hard-shell gelatin capsule.

EXAMPLE XVIII

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the above ingredients, except water, are combined and heated to 60° C. with stirring. A sufficient quantity of water at 60° C. is then added with vigorous stirring to emulsify the ingredients, and water then added q.s. 100 g.

We claim:

1. A method for treating an auto-immune disease, by administering to a subject in need thereof a compound of the formula:

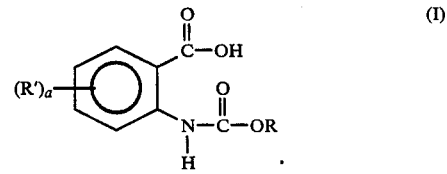

or a pharmaceutically acceptable salt thereof, wherein:
a is an integer of 1 or 2 and R' is in the 6— or 4— position of the benzoic acid ring system.

R is alkyl, phenyl, or cycloalkyl having three to six carbon atoms, wherein the phenyl, or cycloalkyl ring is optionally substituted with 1 to 3 substituents independently selected from the group consisting of lower alkyl having one to four carbon atoms, lower alkoxy having one to four carbon atoms, $-N(R^1)_2$, $-NO_2$, halo, and lower alkylthio having one to four carbon atoms; and each R' is independently selected from the group consisting of lower alkyl having one to six carbon atoms, lower alkenyl having two to six carbon atoms, halo-lower alkyl or lower alkylthio having one to six carbon atoms, halo, and NO₂, in which each R¹ is independently hydrogen or lower alkyl having one to four carbon atoms.

2. The method of claim 1 wherein a is at least one in the compound of Formula (I).

3. The method of claim 2 wherein an R' is in at least one of the 6— and 4— positions in the compound of Formula (I).

4. The method of claim 3 wherein an R' is in both of the 6— and 4— positions in the compound of Formula (I).

5. The method of claim 3 wherein an R' is in the 4— position and the 5— position in the compound of Formula (I).

6. The method of claim 3 wherein an R' is in the 6— position in the compound of Formula (I).

7. The method of claim 6 wherein in the compound of Formula (I) the R'substituent at the 6— position is lower alkyl having one to six carbon atoms or lower alkenyl having two to six carbon atoms.

8. The method of claim 7 wherein in the compound of Formula (I) the R'substituent at the 6— position is lower alkyl having from one to six carbon atoms.

9. The method of claim 8 wherein in the compound of Formula (I) the R'substituent at the 6— position is lower alkyl having from one to three carbon atoms.

10. The method of claim 9 wherein in the compound of Formula (I) the R'substituent at the 6— position is methyl or ethyl.

11. The method of claim 3 wherein an R' is in the 4— position in the compound of Formula (I).

12. The method of claim 11 wherein the R' at the 4— position in the compound of Formula (I) is selected from the group consisting of: hydroxy, lower alkoxy having one to six carbon atoms, NR¹COH,

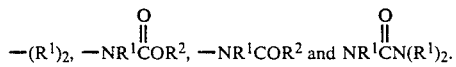

13. The method of claim 12 wherein the R' substituent at the 4— position in the compound of Formula (I) is hydroxy, -N(R¹)₂ or -NR¹COOR².

14. The method of claim 13 wherein in the compound of Formula (I) each R¹ is independently hydrogen, methyl or ethyl, and each R² is independently methyl or ethyl.

15. The method of claim 1, wherein the compound of Formula I is selected from the group consisting of:
2-ethoxycarbonylaminobenzoic acid;
2-benzyloxycarbonylaminobenzoic acid;
2-ethoxycarbonylamino-5-isopropylbenzoic acid;
2-ethoxycarbonylamino-4,5-dimethoxybenzoic acid;
2benzyloxycarbonylamino-4,5-dimethoxybenzoic acid;
2-methoxycarbonylamino-6-methylbenzoic acid;
2-ethoxycarbonylamino-6-methylbenzoic acid;
2-propoxycarbonylamino-6-methylbenzoic acid;
2-isobutoxycarbonylamino-6-methylbenzoic acid;
2-benzyloxycarbonylamino-6-methylbenzoic acid;
2-methoxycarbonylamino-6-ethylbenzoic acid;
2-ethoxycarbonylamino-6-ethylbenzoic acid;
2-propoxycarbonylamino-6-ethylbenzoic acid;
2-methoxycarbonylamino-6propylbenzoic acid;
2-ethoxycarbonylamino-6-propylbenzoic acid; and
2-propoxycarbonylamino-6-propylbenzoic acid.

16. A pharmaceutical composition useful for treating autoimmune diseases, comprising, in admixture with at least one pharmaceutically acceptable excipient, a therapeutically effective amount of a compound of the Formula:

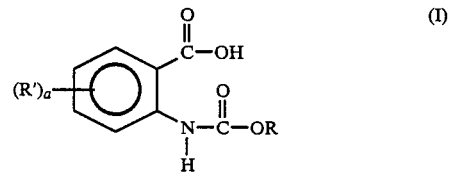

a is an integer of 1 or 2 and R' is in the 6— or 4— position of the benzoic acid ring system.

R is alkyl, phenyl, or cycloalkyl having three to six carbon atoms, wherein the phenyl, or cycloalkyl ring is optionally substituted with 1 to 3 substituents independently selected from the group consisting of lower alkyl having one to four carbon atoms, lower alkoxy having one to four carbon atoms, —N(R¹)₂, —NO₂, halo, and lower alkylthio having one to four carbon atoms; and each R' is independently selected from the group consisting of lower alkyl having one to six carbon atoms, lower alkenyl having two to six carbon atoms, halo-lower alkyl or lower alkylthio having one to six carbon atoms, halo, and NO₂, in which each R¹ is independently hydrogen or lower alkyl having one to four carbon atoms. form a piperidine or piperazine ring optionally substituted at the ring nitrogen with lower alkyl having one to four carbon atoms or —CH₂CH₂OH; each R² is independently lower alkyl having one to four carbon atoms in the compound of Formula (I).

17. The composition of claim 16 wherein a is at least one in the compound of Formula (I).

18. The composition of claim 17 wherein an R' is in at least one of the 6- and 4- positions of the compound of Formula (I).

19. The composition of claim 18 wherein an R' is in both of the 6- and 4- positions of the compound of Formula (I).

20. The composition of claim 19 wherein an R' is in the 4- position and the 5- position of the compound of Formula (I).

21. The composition of claim 20 wherein an R' is in the 6- position of the compound of Formula (I).

22. The composition of claim 21 wherein in the compound of Formula (I) the R' substituent at the 6-position is lower alkyl having one to six carbon atoms or lower alkenyl having two to six carbon atoms.

23. The composition of claim 22 wherein in the compound of Formula (I) the R' substituent at the 6-position is lower alkyl having from one to six carbon atoms.

24. The composition of claim 23 wherein in the compound of Formula (I) the R' substituent at the 6-position is lower alkyl having from one to three carbon atoms.

25. The composition of claim 24 wherein the R' substituent at the 6- position is methyl or ethyl in the compound of Formula (I).

26. The composition of claim 18 wherein an R' is in the 4- position in the compound of Formula (I).

27. The composition of claim 26 wherein in the compound of Formula (I) the R' at the 4- position is selected from the group consisting of: hydroxy, lower alkoxy having one to six carbon atoms, NR$^1$COH, —N(R$^1$)$_2$, —NR$^{10}$COR$^2$, —NR$^1$COR$^2$ and NR$^{10}$CN(R$^1$)$_2$.

28. The composition of claim 27 wherein the R' substituent at the 4— position of the compound of Formula (I) is hydroxy, —N(R$^1$)$_2$ or —NR$^1$COOR$^2$.

29. The composition of claim 28 wherein in the R' substituent at the 4— position of the compound of Formula (I), each R$^1$ is independently hydrogen, methyl or ethyl, and each R$^2$ is independently methyl or ethyl 30. The composition of claim 16, wherein the compound of Formula I is selected from the group consisting of:
2-ethoxycarbonylaminobenzoic acid;
2-benzyloxycarbonylaminobenzoic acid;
2-ethoxycarbonylamino-5-isopropylbenzoic acid;
2-ethoxycarbonylamino-4,5-dimethoxybenzoic acid;
2-benzyloxycarbonylamino-4,5-dimethoxybenzoic acid;
2-methoxycarbonylamino-6-methylbenzoic acid;
2-ethoxycarbonylamino-6-methylbenzoic acid;
2-propoxycarbonylamino-6-methylbenzoic acid;
2-isobutoxycarbonylamino-6-methylbenzoic acid;
2-benzyloxycarbonylamino-6-methylbenzoic acid;
2-methoxycarbonylamino-6-ethylbenzoic acid;
2-ethoxycarbonylamino-6-ethylbenzoic acid;
2-propoxycarbonylamino-6-ethylbenzoic acid;
2-methoxycarbonylamino-6-propylbenzoic acid;
2-ethoxycarbonylamino-6-propylbenzoic acid; and
2-propoxycarbonylamino-6-propylbenzoic acid.

* * * * *